(12) United States Patent
Lim et al.

(10) Patent No.: US 10,782,234 B2
(45) Date of Patent: Sep. 22, 2020

(54) COMPOSITION FOR DETECTING BLOODSTAIN

(71) Applicants: Korean National Police Agency, Seoul (KR); Republic of Korea(National Forensic Service Director Ministry of Interior and Safety), Wonju-si, Gangwon-do (KR)

(72) Inventors: Seung Lim, Changwon-si (KR); Si-Keun Lim, Wonju-si (KR)

(73) Assignees: Korean National Police Agency, Seoul (KR); Republic of Korea(National Forensic Service Director Ministry of Interior and Safety), Wonju-si (KR)

( * ) Notice: Subject to any disclaimer, the term of this patent is extended or adjusted under 35 U.S.C. 154(b) by 189 days.

(21) Appl. No.: 16/009,750

(22) Filed: Jun. 15, 2018

(65) Prior Publication Data

US 2018/0364170 A1 Dec. 20, 2018

(30) Foreign Application Priority Data

Jun. 16, 2017 (KR) .................... 10-2017-0076900

(51) Int. Cl.
| | | |
|---|---|---|
| *G01N 21/64* | (2006.01) | |
| *C12Q 1/6806* | (2018.01) | |
| *C12Q 1/68* | (2018.01) | |
| *G01N 21/76* | (2006.01) | |

(52) U.S. Cl.
CPC ....... *G01N 21/6428* (2013.01); *C12Q 1/6806* (2013.01); *G01N 21/76* (2013.01); *G01N 2021/6439* (2013.01)

(58) Field of Classification Search
CPC .. G01N 21/6428; G01N 21/64; C12Q 1/6806; C12Q 1/68; C12Q 1/00
USPC ........................................... 436/63
See application file for complete search history.

(56) References Cited

U.S. PATENT DOCUMENTS

| | | | | |
|---|---|---|---|---|
| 5,976,886 A | * | 11/1999 | Cheeseman | G01N 21/6447 356/39 |
| 6,692,967 B1 | * | 2/2004 | Di Benedetto | G01N 21/6447 356/39 |
| 2005/0176082 A1 | * | 8/2005 | Lefebvre-Despeaux | G01N 33/725 435/8 |
| 2012/0083038 A1 | * | 4/2012 | Eversdijk | G01N 21/6428 436/94 |

FOREIGN PATENT DOCUMENTS

| | | |
|---|---|---|
| KR | 100679386 B1 | 1/2007 |
| KR | 1020120132246 A | 12/2012 |
| KR | 1020140117378 A | 10/2014 |

OTHER PUBLICATIONS

Cheyne, Morgan, Illuminating Latent Blood, Application methods, fixatives, alternatives and new formulas for luminol, 2011, The University of Auckland, pp. 1-222. (Year: 2011).*

* cited by examiner

*Primary Examiner* — Christine T Mui
(74) *Attorney, Agent, or Firm* — Novick, Kim & Lee, PLLC; Jae Youn Kim

(57) ABSTRACT

A composition for detecting a bloodstain includes: 3-aminophthalhydrazide; glycine; sodium hydroxide; and sodium phosphate dibasic heptahydrate.

5 Claims, 25 Drawing Sheets

| | blood dilution ratio | | | | |
|---|---|---|---|---|---|
| | 1:10 | 1:100 | 1:1,000 | 1:10,000 | 1:100,000 |
| whole blood | | | | | |
| BlueStar® | | | | | |
| Luminol | | | | | |
| L | | | | | |
| L-MS0.3 | | | | | |
| L-MS1.0 | | | | | |
| L-PPT2 | | | | | |
| L-PPT10 | | | | | |
| L-SS2 | | | | | |
| L-SS10 | | | | | |

FIG. 12a

|            | blood dilution ratio | | | | |
|---|---|---|---|---|---|
|            | 1:10 | 1:100 | 1:1,000 | 1:10,000 | 1:100,000 |
| whole blood | | | | | |
| BlueStar® | | | | | |
| Luminol | | | | | |
| L | | | | | |
| L-MS0.3 | | | | | |
| L-MS10 | | | | | |
| L-PPT2 | | | | | |
| L-PPT10 | | | | | |
| L-SS2 | | | | | |
| L-SS10 | | | | | |

FIG. 12b

| | blood dilution ratio | | | | |
|---|---|---|---|---|---|
| | 1:10 | 1:100 | 1:1,000 | 1:10,000 | 1:100,000 |
| whole blood | | | | | |
| BlueStar® | | | | | |
| Luminol | | | | | |
| L | | | | | |
| L-MS0.3 | | | | | |
| L-MS1.0 | | | | | |
| L-PPT2 | | | | | |
| L-PPT10 | | | | | |
| L-SS2 | | | | | |
| L-SS10 | | | | | |

FIG. 12c

|  | blood dilution ratio | | | | |
| --- | --- | --- | --- | --- | --- |
|  | 1:10 | 1:100 | 1:1,000 | 1:10,000 | 1:100,000 |
| whole blood | | | | | |
| BlueStar® | | | | | |
| Luminol | | | | | |
| L | | | | | |
| L-MS0.3 | | | | | |
| L-MS1.0 | | | | | |
| L-PPT2 | | | | | |
| L-PPT10 | | | | | |
| L-SS2 | | | | | |
| L-SS10 | | | | | |

FIG. 12d

COMPOSITION FOR DETECTING BLOODSTAIN

CROSS-REFERENCE TO RELATED APPLICATIONS

This application claims priority to KR 10-2017-0076900, filed Jun. 16, 2017, the disclosure of which is incorporated by reference herein in its entirety.

BACKGROUND OF THE INVENTION

1. Field of the Invention

The present invention relates to a composition for detecting a bloodstain.

2. Description of the Related Art

It is very important to find out an invisible bloodstain at an accident site or a bloodstain on a suspect, a victim, a specific object, a vehicle or the like, and taking and preserving the bloodstain in an appropriate way serves as an important role to reconstruct the incident and further identify the suspect.

Various reagents have been developed and used in fields to distinguish whether a blood is present and find out the invisible bloodstain, and Luminol may be the most representative reagent.

Since the publication of research thesis by Grodsky in 1951 and Weber in 1966 on chemiluminescence of the Luminol in reaction with a bloodstain, various fabrication methods have been studied to increase the luminescence intensity and reduce the error response.

Bluestar forensic (hereinafter referred to as "Bluestar") is a product that remarkably improved the weak luminescence intensity, the short luminescence time, and the like of the existing Luminol reagents. Developers announced that the storage of the Luminol reagent was improved by adding carbamide peroxide instead of hydrogen peroxide as an oxidant. Currently, Bluestar is used in most criminal investigation agencies because of the ease of preparation and the prevention of bloodstain DNA from being destroyed.

Bluestar has a problem of the utilization in the field due to a high preparation cost per unit volume because Bluestar is imported as a finished product.

DOCUMENT OF RELATED ART (Patent Document 1) Korean Patent Registration No. 10-0679386 (Registered in Jan. 30, 2007)
(Patent Document 1) Korean Patent Registration No. 10-2014-0117378 (Published in Oct. 7, 2014)
(Patent Document 3) Korean Patent Registration No. 10-2012-0132246 (Published in Dec. 5, 2012)

SUMMARY OF THE INVENTION

The present invention is provided to fabricate a new type Luminol reagent improved in the luminescence intensity for a bloodstain and the luminescence duration after reaction, and reduce preparation costs.

The composition for detecting a bloodstain according to the present invention includes: 3-aminophthalhydrazide, glycine as a pH adjusting agent, sodium hydroxide as an alkaline substance, and sodium phosphate dibasic heptahydrate as a pH stabilizer.

The composition for detecting a bloodstain may have hydrogen ion concentration (pH) of 12.0 or less. Specifically, the hydrogen ion concentration (pH) may be 11.9 to 12.0. More specifically, the hydrogen ion concentration (pH) may be 11.3 to 11.7.

In one example, the composition for detecting a bloodstain may further include hydrogen peroxide and magnesium sulfate heptahydrate.

In another example, the composition for detecting a bloodstain may further include sodium borate monohydrate, in which the concentrations of the hydrogen peroxide and the magnesium sulfate heptahydrate may be 0%.

The composition for detecting a bloodstain according to the present invention has a high sensitivity to the bloodstain diluted by 1:10,000 and has a high luminescence intensity, so that a dark room is unnecessary upon photographing.

The composition for detecting a bloodstain according to the present invention prevents blood DNA from being destroyed, so that the composition can rarely exert a particular effect on DNA identity confirmation.

The composition for detecting a bloodstain according to the present invention has an excellent stability, so that the composition can be used for more than 7 days after preparation of a reagent, and particularly, the preparation cost per unit volume can be about 10 times lower than that of Bluestar.

BRIEF DESCRIPTION OF THE DRAWINGS

FIGS. 12a to 12d are images showing changes of the bloodstain sensitivity due to storage of a Luminol reagent.

DETAILED DESCRIPTION OF THE INVENTION

Figure 1:
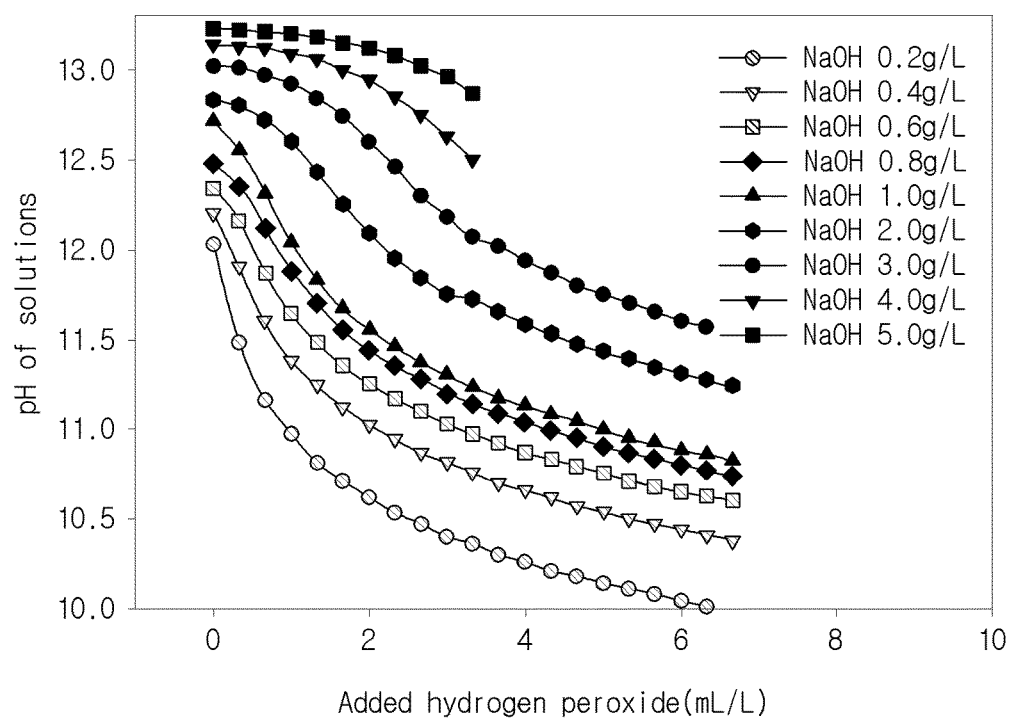
FIG. 1 is a graph showing pH changes of an aqueous solution of sodium hydroxide caused by adding hydrogen peroxide.

Hereinafter, the present invention will be described in further detail with reference to drawings and examples.

Inventors confirmed the effects on the sensitivity, the sensitivity changes during storage, the bloodstain specificity, and the luminescence persistence of a Luminol reagent by adding a hydrogen peroxide stabilizer, and confirmed the possibility of using sodium perborate instead of hydrogen peroxide as an oxidant.

The bloodstain sensitivity and the luminescence intensity of Luminol are dependent on pH of a prepared reagent. Although it may be preferable to use sodium hydroxide rather than sodium carbonate for fabrication, a strong alkaline aqueous solution may exert an effect on bloodstain DNA. Thus, pH is required to be adjusted.

The inventors adjusted pH by adding glycine, and the addition of glycine had no effect on the bloodstain sensitivity and the luminescence intensity. It is preferable to determine the added amount based on a pH change of the reagent after bloodstain reaction rather than pH of the Luminol reagent at the time of fabrication.

When a hydrogen peroxide stabilizer was not added upon preparation of the Luminol reagent, weak luminescence was continuously observed in the prepared reagent. This is presumed to be the oxidation of Luminol due to the degradation of hydrogen peroxide in an alkaline aqueous solution. The above phenomenon did not occur because the addition of magnesium sulfate heptahydrate upon preparation of the Luminol reagent increases the stabilization of hydrogen peroxide. In addition, the addition of magnesium sulfate heptahydrate did not exert any effect on the sensitivity to bloodstains, and pH of the reagent was stabilized and the storage period was significantly increased when at least 0.1 g/L was added. Although potassium phosphate tribasic and sodium silicate showed similar tendencies, they may be unsuitable for use in actual reagent preparation because excessive amounts are required during preparation and they are less inefficient than magnesium sulfate heptahydrate.

In the case of HEIDA, although pH of the Luminol reagent was stabilized by small amount addition, HEIDA may not be independently used unlike other stabilizers because HEIDA decreases pH of the reagent and affects the bloodstain sensitivity.

In the case of Bluestar, although pH of the reagent did not change during storage, it was presumed to have a different reaction mechanism compared to the Luminol reagents, because the bloodstain reactivity completely disappeared within 3 days.

It was found that the storage period is closely related to a pH change of the reagent, based on the changes of the bloodstain sensitivity during storage after preparation of the reagent. Since it is determined that the pH change of the reagent is related to the degradation of hydrogen peroxide, as a result, it seems that the addition of the hydrogen peroxide stabilizer is directly related to the bloodstain sensitivity and the storage period of the reagent.

The addition of the hydrogen peroxide stabilizer did not significantly exert an effect on the blood specificities of the Luminol reagents. It is presumed that the weak luminescences observed in some vegetables are caused by a mechanism due to peroxidase, and the strong luminescences in metal salts and bleaches are resulted from the rapid degradation of hydrogen peroxide by metal ions or sodium hypochlorite.

It was found that there was just a difference in the luminescence intensity and no significant difference in the bloodstain specificity because the reagent has the same mechanism in reacting with a substance even when the fabrication method is changed.

The luminescence duration after reaction with bloodstains is very important factor for a site investigation such as photographing. The Luminol reagent prepared by adding magnesium sulfate as a stabilizer had a longer luminescence duration of average 20 seconds compared to Bluestar, but the Luminol reagent prepared by adding HEIDA to the same reagent had the lower luminescence intensity and the shorter luminescence duration.

As a result, it was found that the luminescence duration may be increased by developing a fabrication method for increasing the luminescence intensity upon bloodstain reaction. It was confirmed that pH was closely related to the destruction of bloodstain DNA, based on a preliminary experiment. Although an exact pH range causing the destruction of bloodstain DNA is unknown, it is determined that pH is 12.2 or less based on the results of previous researches.

Figure 3:
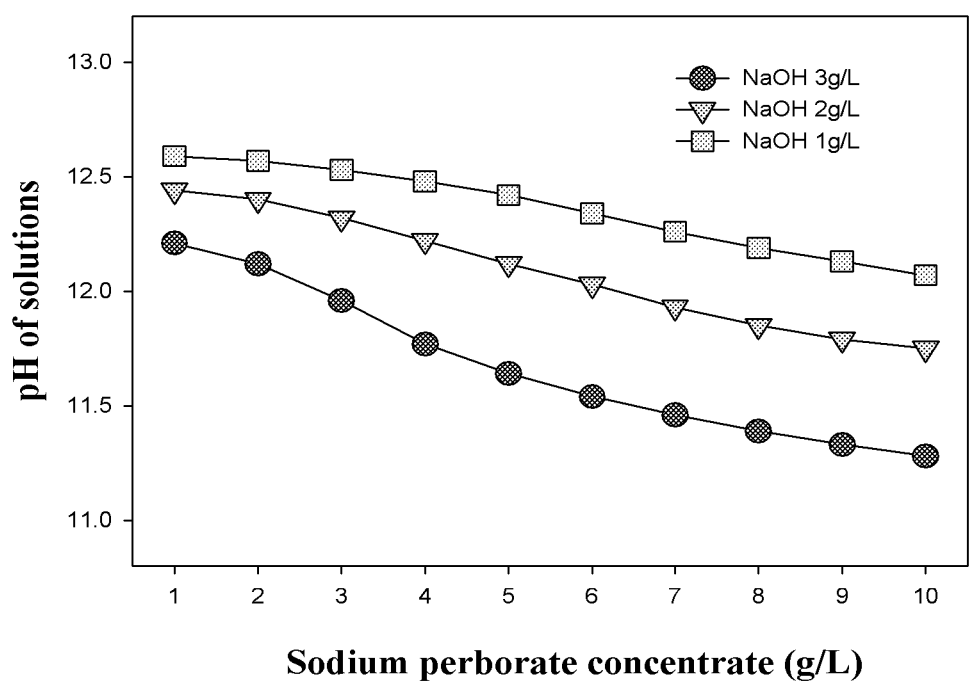
FIG. 3 is a graph showing pH changes of an aqueous solution of sodium hydroxide caused by adding sodium perborate.

Whereas the pH increase of Bluestar was small after blood reaction, the pH increases of the Luminol reagents were high around 0.6, but pH of each Luminol reagent is 12.0 or less. Thus, it is presumed that the Luminol reagents may not exert a significant effect on DNA. On the other hand, in the case that sodium perborate is used as an oxidant, the pH increase was much lower than when hydrogen peroxide was used, which corresponds to the results that sodium perborate exerts less effect on pH of the Luminol reagent than hydrogen peroxide does (FIGS. 1 and 3). As a result, when the added amount of glycine is reduced upon preparation of the reagent, the luminescence intensity to the bloodstain may be increased.

When the amount of blood used in the reaction increases, pH changes of a mixed solution after the reagent is reacted with the blood becomes greater. It is preferable to use sodium perborate instead of hydrogen peroxide as an oxidant at the time of preparing the Luminol reagent so as to inhibit the pH changes. In addition, it is preferable to add sodium phosphite dibasic so as to minimize the pH changes after reaction.

Materials and Instruments for Experiment

Sodium hydroxide (NaOH), potassium phosphate tribasic ($K_3PO_4$), magnesium sulfate heptahydrate ($MgSO_4.7H_2O$), sodium silicate ($Na_2SiO_3$), and sodium carbonate ($Na_2CO_3$) were purchased from Duksan Chemicals Inc., Korea.

Hydrogen peroxide ($H_2O_2$), glycine, sodium perborate monohydrate ($NaBO_3.H_2O$, SPB), and sodium phosphate dibasic ($Na_2HPO_4.7H_2O$, SPD) were purchased from ACROS (Sigma, USA).

Luminol (3-aminophthalhydrazide) was used from a product of Samcheon Chemical (Korea).

Bluestar was purchased from IDTech's Bluestar Forensic (Sirchie finger print laboratories, Inc., USA).

In addition, a paper disc (10 mm, ADVATEC), a vortex mixer (KMC-1300V, Vision), a precision balance (HS300A, Hansung Instrument Industry), and a pH meter (pH-200L, iSTEK) were used in the experiments.

Methods for Experiments

All blood used in the experiments were obtained with the consents of volunteers, put in an EDTA tube, used while being stored in a refrigerator set at 4° C., and discarded after 30 days of extraction.

(Preparation of Diluted Blood Sample)

A dilution multiple is the ratio of blood to total volume. A 1:10 diluted blood solution was prepared by adding 9 mL of distilled water to 1 mL of blood. A 1:100 diluted blood solution was prepared by adding 1 mL of 1:10 to 9 mL of distilled water. In the same manner, diluted blood solutions were prepared by 1:1,000, 1:10,000, and 1:100,000. After every 100 µl of the diluted blood solution was dropped on a paper disc by using a micropipette, and dried at room temperature for more than 8 hours to prepare a diluted blood sample for the experiment.

(Preparation of Reagent)

Comparative Example 1: Bluestar forensic

One tablet of beige Bluestar and one tablet of white Bluestar were mixed with 125 mL of sterilized distilled water.

Comparative Example 2: Luminol reagent prepared by a method used in the Korean National Police Agency (KNPA)

1 g/L of Luminol, 50 g/L of sodium carbonate, 150 mL of 30% (w/v) hydrogen peroxide, and 1 L of distilled water.

Examples 1 to 6: Luminol reagents prepared by a Luminol preparation method (L-type: modified Weber method)

Basic composition: 1 g/L of Luminol, 3 g/L of sodium hydroxide, 1 g/L of glycine, 10 ml/L of hydrogen peroxide, and 1 L of distilled water Examples 1 to 6 were prepared by adding a hydrogen peroxide stabilizer to the above basic composition as follows Example 1

L-MS0.3: L type, and 0.3 g/L of magnesium sulfate tetrahydrate

Example 2

L-MS1.0: L type, and 1.0 g/L of magnesium sulfate tetrahydrate

Example 3

L-PPT2: L type, and 2.0 g/L of potassium phosphate tribasic,

Example 4

L-PPT10: L type, and 10 g/L of potassium phosphate tribasic,

Example 5

L-SS2: L type, and 2.0 g/L of sodium silicate

Example 6

L-SS10: L type, and 10 g/L of sodium silicate

Example 7: Luminol reagent prepared by a Luminol preparation method (L-SPB type)

1 g/L of Luminol, 3 g/L of sodium hydroxide, 2 g/L of glycine, and 10 g/L of sodium perborate monohydrate (pH Measurement)

pH-200L (Istek, Korea) was used to check an effect of the reagents added at the time of preparation on pH of the Luminol reagents, and to check final pH of the prepared reagents. In addition, pH of Bluestar sold in the form of a finished product was measured by using the same equipment after the reagents were prepared.

(Photographing Condition)

A dark room was used to check the luminescence intensity and the luminescence duration of the Luminol reagents. Each 100 µl of Luminol reagents was dropped on the diluted bloodstain samples prepared by the above method, and observed and photographed. The photographing condition of a camera Cannon EOS70D was fixed at ISO 400, F11, S30" to compare the luminescence intensity under the same conditions.

pH Changes of Sodium Hydroxide Solution by Adding Oxidant

Because pH of the Luminol reagenta serves an important factor in order to dissolve Luminol and induce strong chemical luminescence upon reaction with bloodstains, pH changes of aqueous solutions by sodium hydroxide, hydrogen peroxide, and sodium perborate were checked.

In order to check pH changes due to the addition of hydrogen peroxide, a sodium hydroxide concentration was adjusted to 0.2 to 5.0 g/L, and then pH changes of the aqueous solution were measured while a predetermined amount of 30% (w/v) hydrogen peroxide being added.

In the case of sodium perborate, after 1.0, 2.0 and 3.0 g/L of a sodium hydroxide aqueous solution was prepared, pH changes of the aqueous solution were measured while sodium perborate was added from 0 to 10.0 g/L by 1.0 g/L.

The biggest factor exerting an effect on pH of the reagents was sodium hydroxide, and an alkaline aqueous solution having about pH 12.0 was prepared by adding 0.2 g/L or more.

As shown in FIG. 1, although hydrogen peroxide used as an oxidant also exerts an effect on pH of the Luminol reagents, the effect is smaller than sodium hydroxide does. In other words, when the added amount of sodium hydroxide increases, the amount of hydrogen peroxide added to adjust pH of the reagents is required to be exponentially increased.

It may not be preferable to prepare the Luminol reagent by adding at least 3 g/L of sodium hydroxide if a substance capable of adjusting pH is not added when the reagent is prepared.

In order to check the effect of glycine added when the Luminol reagent was prepared, 1.0 and 3.0 g/L of a sodium hydroxide aqueous solution were prepared and then pH changes of the aqueous solution were observed and recorded while glycine being added by unit of 0.2 g/L.

Figure 2:
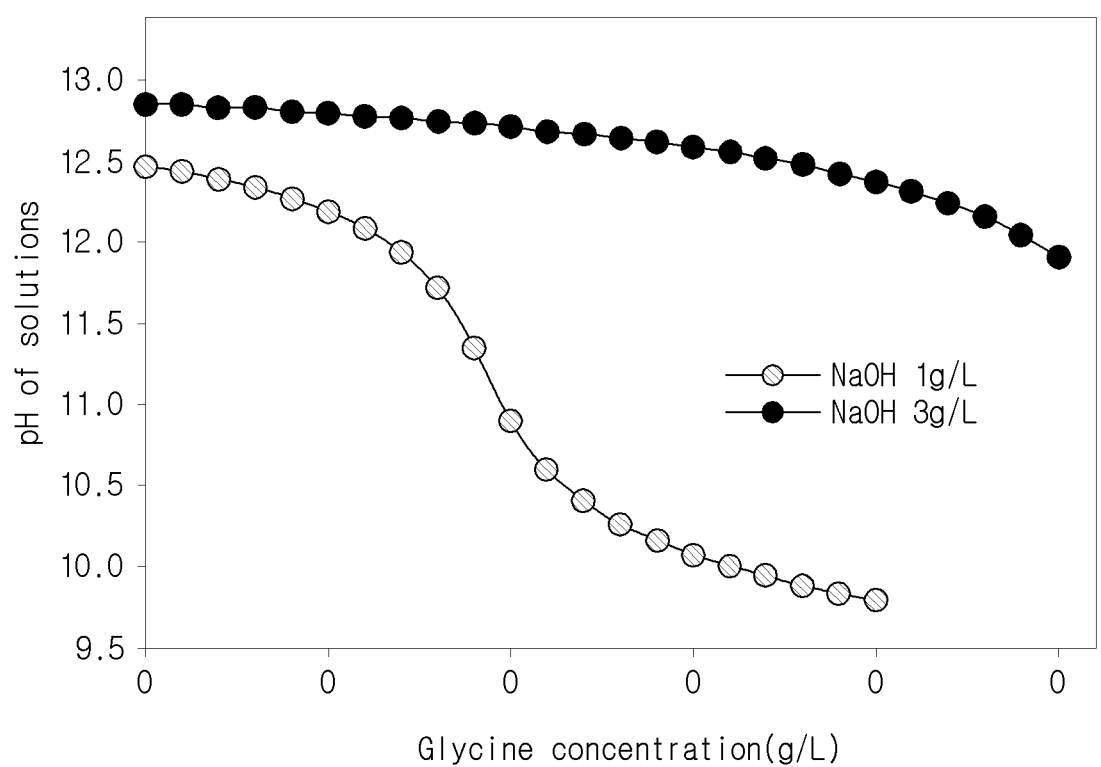
FIG. 2 is a graph showing pH changes of an aqueous solution of sodium hydroxide caused by adding glycine.

Glycine, which is one of amino acids and has been reported that the luminescence intensity of the Luminol reagent is lowered by sodium hypochlorite, was used as a pH adjusting agent for the Luminol reagent. Similarly to sodium hydroxide and hydrogen peroxide, the addition of glycine changed pH of the Luminol reagent (FIG. 2). Because there was a point where pH of the solution was rapidly lowered by adding 1.0 to 2.0 g/L of glycine subject to 1.0 g/L of the sodium hydroxide concentration, attention is required for preparing the Luminol reagent, and the added amount may be required to be adjusted according to the final pH.

When sodium perborate is used instead of hydrogen peroxide as an oxidant, it was also found that pH of the sodium hydroxide aqueous solution changed as the added amount was increased. As shown in FIG. 3, it was found that the added amount was required more compared to hydrogen peroxide to adjust pH of the Luminol reagent to a desired level (pH 11.4 to 11.6). In other words, when sodium perborate is used as an oxidant upon preparing the Luminol reagent, the added amount of glycine may be required to be increased more than sodium perborate to adjust pH of the reagent.

Effect of Addition of Glycine on Bloodstain Sensitivity of Luminol Reagent

After glycine was added to the above-described L-MS 1.0 formulation at a concentration of 0 g/L, 1.0 g/L, 2.0 g/L, and 3.0 g/L to prepare reagents, the bloodstain sensitivity was measured by using 1:10 to 1:10,000 diluted bloodstain samples.

Because pH of the reagent decreases as the added amount of glycine increases, the Luminol reagents were equally adjusted to have pH 11.4 by using an aqueous solution of sodium hydroxide (10%, w/v) so as to exclude the effect by pH.

Figure 4:
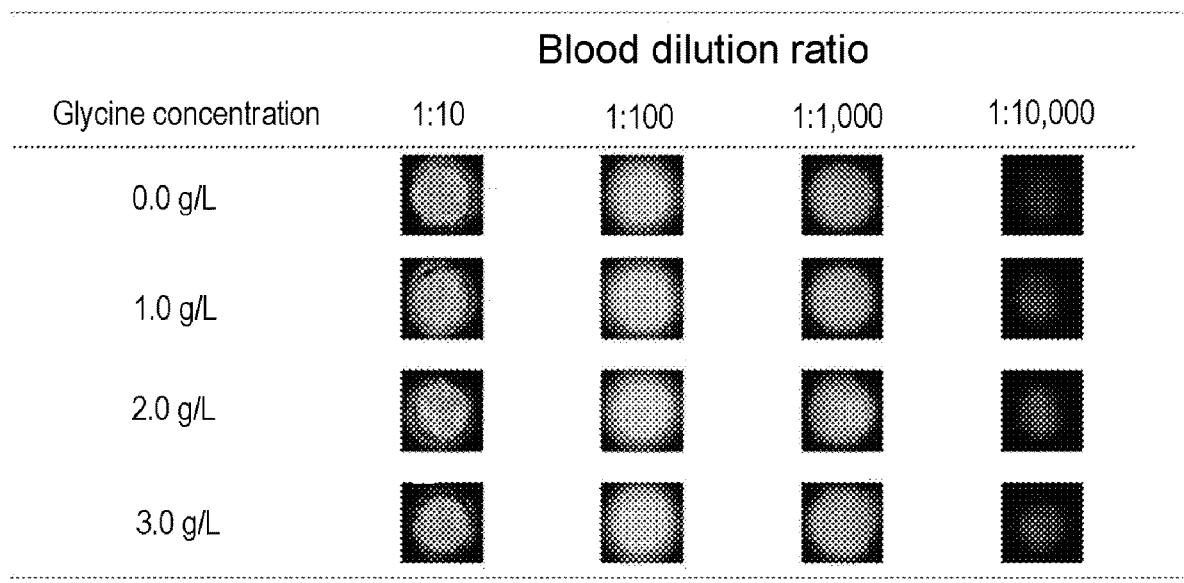
FIG. 4 is an image showing changes of bloodstain sensitivity of a Luminol reagent according to the concentration of glycine.

FIG. 4 shows the results of reacting each of the Luminol reagents with 1:10 to 1:10,000 diluted bloodstain samples. Referring to FIG. 4, it was found that the sensitivity to diluted bloodstains was similar at the same pH conditions regardless of the amount of glycine. Of course, because pH of the Luminol reagent decreases as the added amount of glycine increases when pH is not adjusted, the sensitivity to diluted bloodstain may be lowered.

pH Changes During Storage of Luminol Reagent According to Addition of Hydrogen Peroxide Stabilizer Although most of liquid hydrogen peroxide sold on the market contains phosphate to inhibit a degradation, the liquid hydrogen peroxide merely shows the effect at neutral pH, but cannot prevent hydrogen peroxide from being degraded in an alkaline aqueous solution. Because the luminescence intensity and the sensitivity with respect to bloodstains of the reagent are significantly deteriorated and pH rises when hydrogen peroxide added upon preparation of the Luminol reagent is gradually degraded, a negative impact may be exerted on a blood DNA analysis.

The Luminol reagent was prepared by using sodium hydroxide, which is a strong alkali substance, instead of sodium carbonate in order to slow the degradation of hydrogen peroxide and increase the storage period of the Luminol reagent.

Because hydrogen peroxide is unstable under alkaline conditions, magnesium sulfate heptahydrate (MS), potassium phosphate tribasic, sodium silicate, and HEIDA (n-(2-hydroxyethyl) iminodiacetic acid), which are commercially sold as a hydrogen peroxide stabilizer, were selected and used.

After the hydrogen peroxide stabilizer was added at a predetermined concentration upon preparation of the reagent, pH changes of the reagent were measured and recorded as time passed while the reagent being stored in a refrigerator (2).

Figure 5:
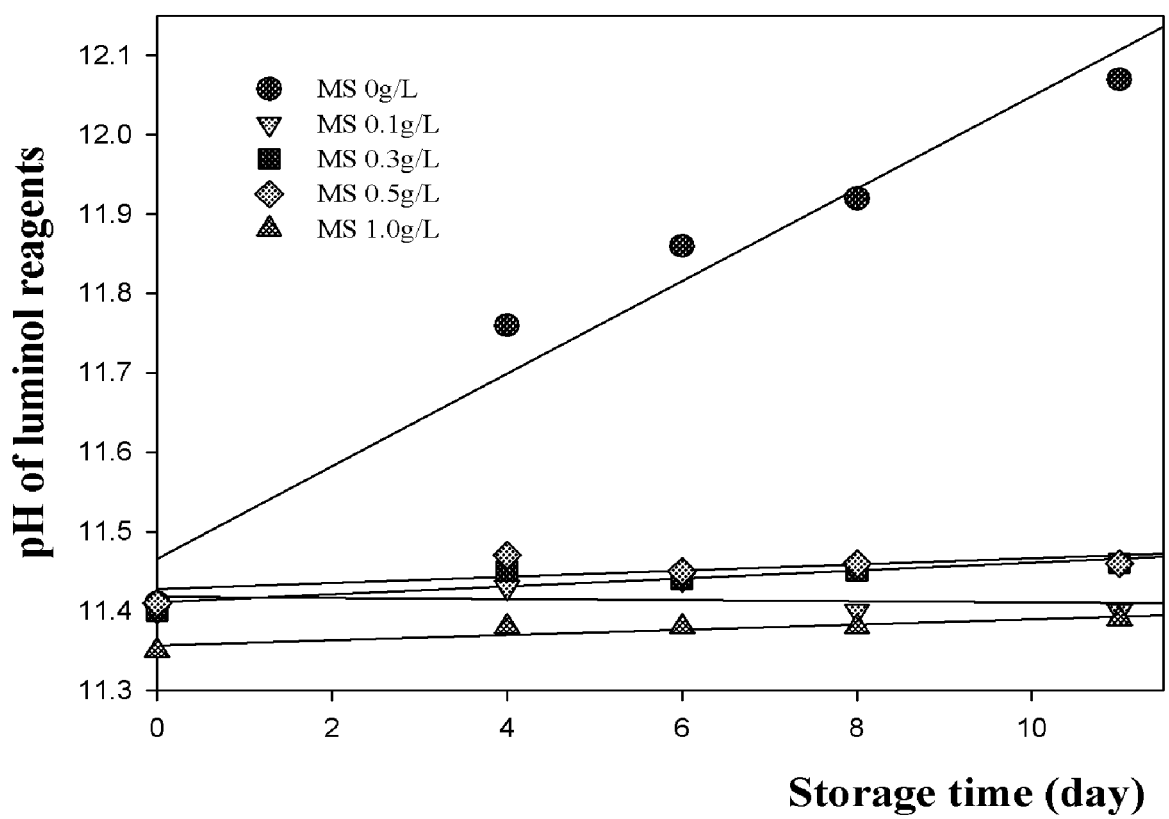
FIG. 5 is a graph showing pH changes of a Luminol reagent during storage caused by adding magnesium sulfate heptahydrate.

Magnesium sulfate heptahydrate did not cause an error reaction of the Luminol reagent despite inclusion of magnesium bivalent cations. As shown in FIG. 5, because hydrogen peroxide was inhibited from being degraded after the addition of 0.1 g/L, pH of the reagent was stabilized, and pH even after stored for 11 days was 11.40 the same as pH of the preparation. Even when the added concentration of magnesium sulfate was increased, pH of the Luminol reagent was constantly maintained during storage, but the amount of magnesium sulfate undissolved upon preparation of the reagent was increased and pH of the reagent was slightly lowered.

When pH of the Luminol reagent is lowered, the sensitivity to bloodstains is decreased. Accordingly, it was determined that the optimum added amount of magnesium sulfate may be 0.1 to 0.5 g/L. The Luminol reagent prepared without adding the hydrogen peroxide stabilizer had pH which was increased to 12.0 or more after storage for 11 days, in which it is presumed that pH was increased due to the degradation of hydrogen peroxide because hydrogen peroxide is only the factor, among the substances added upon preparation of the reagent, capable of exerting an effect on pH of the reagent.

Figure 6:
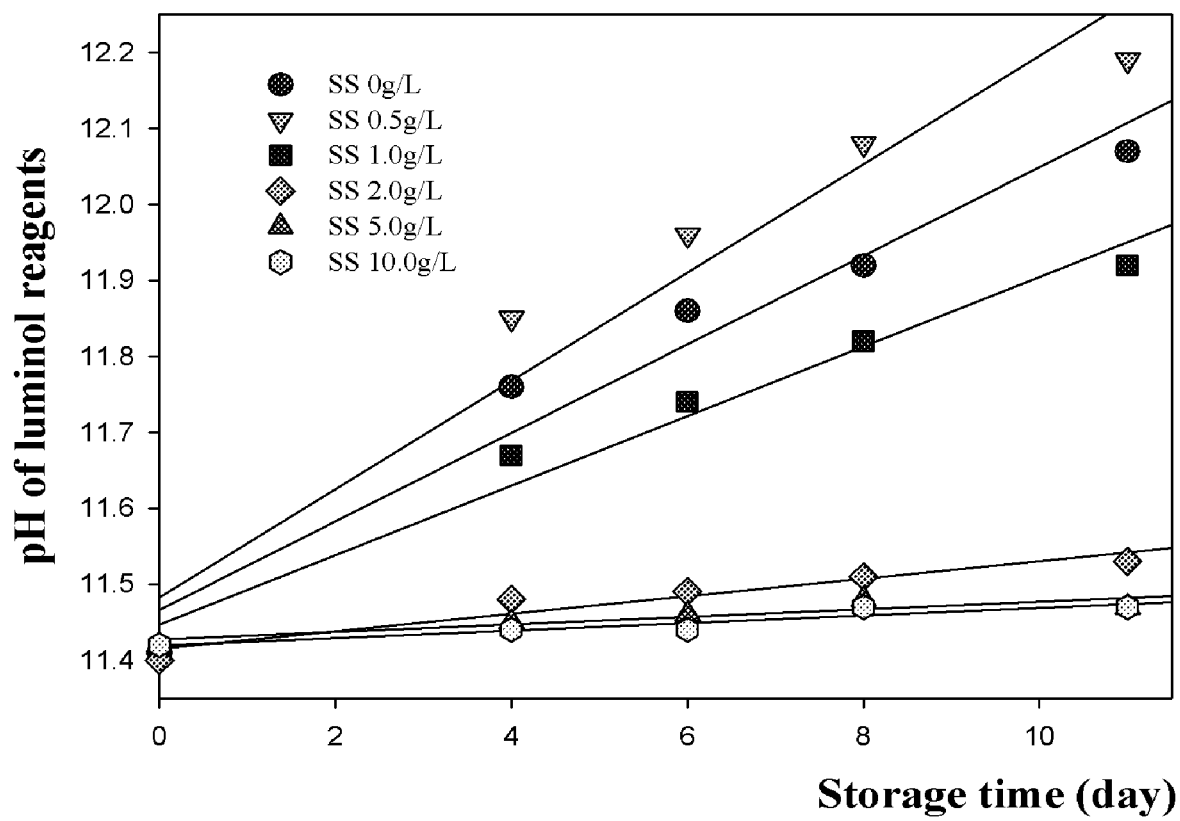
FIG. 6 is a graph showing pH changes of a Luminol reagent during storage caused by adding sodium silicate.

When sodium silicate was added as a hydrogen peroxide stabilizer, the degradation of hydrogen peroxide was rather accelerated at the added amount of 0.5 g/L or less, but the degradation of hydrogen peroxide at a higher concentration was inhibited in proportion to the added amount (FIG. 6).

When the Luminol reagent prepared by adding 10.0 g/L of sodium silicate was stored for 11 days, pH was 11.8 or more. Accordingly, the use of sodium silicate as a hydrogen peroxide stabilizer when the Luminol reagent is prepared may not be effective.

Figure 7:
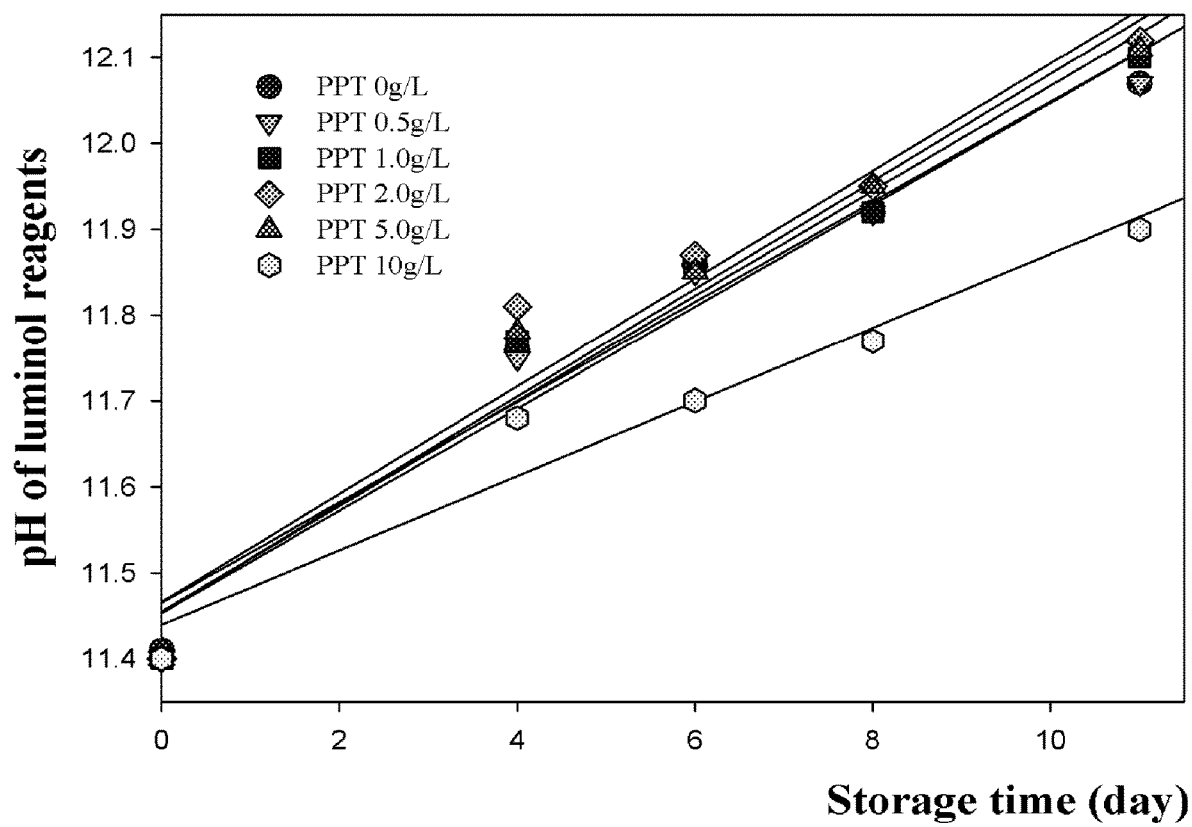
FIG. 7 is a graph showing pH changes of a Luminol reagent during storage caused by adding potassium phosphate tribasic.

When 5.0 g/L or less of potassium phosphate tribasic was added to the Luminol reagent as a hydrogen peroxide stabilizer, pH changes was similar to that of the reagent prepared without adding the stabilizer as time passed. When potassium phosphate tribasic was added at 10.0 g/L, the incremental rate of pH of the Luminol reagent was slightly decreased, but the incremental rate after storage for 8 days became higher than pH 11.40 at the time of fabrication by 0.47 (FIG. 7). It was found that potassium triphosphate tribasic was ineffective to be used as a hydrogen peroxide stabilizer for the Luminol reagent.

Figure 8:
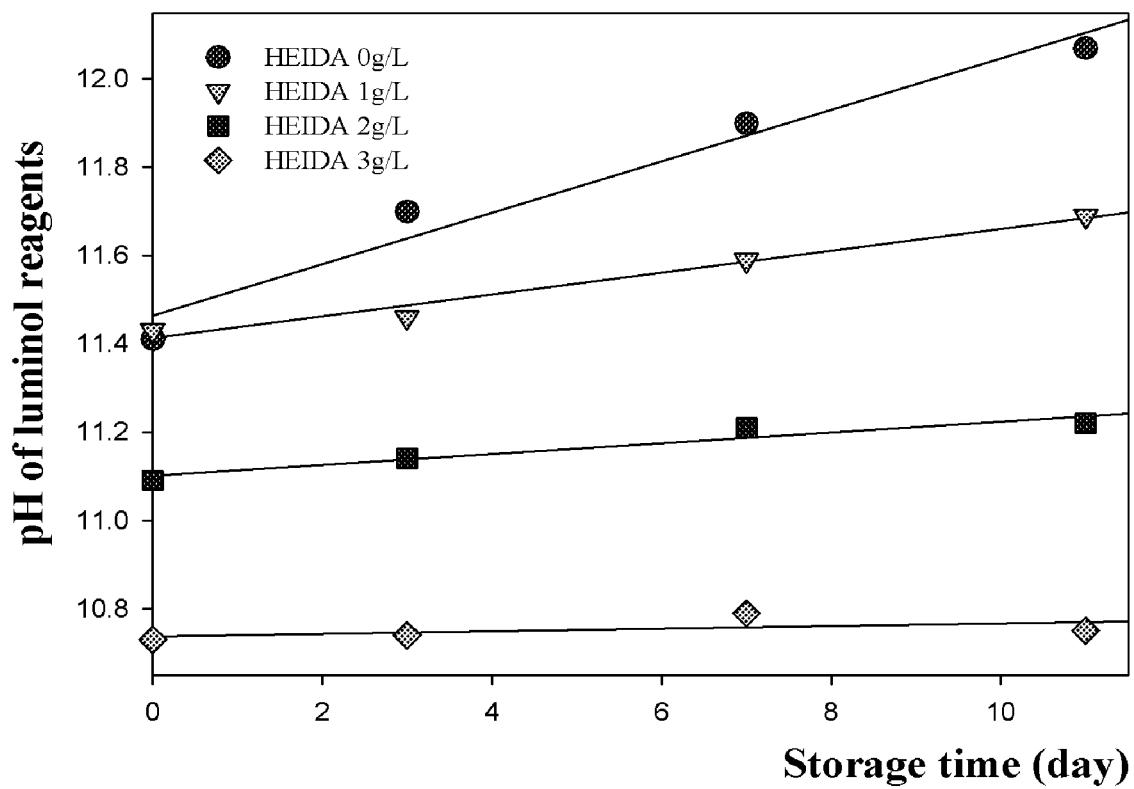
FIG. 8 is a graph showing pH changes of a Luminol reagent during storage caused by adding HEIDA (n-(2-hydroxyethyl)iminodiacetic acd).

FIG. 8 shows pH changes of the reagent during storage when HEIDA was added to the Luminol reagent as a hydrogen peroxide stabilizer. As the HEIDA concentration was increased from 1.0 g/L to 3.0 g/L, pH of the solution was stabilized. At least 2.0 g/L is required to be added for the inhibition at the level of magnesium sulfate in an aqueous alkaline solution. However, when the added amount is increased, pH of the prepared Luminol reagent is decreased, so that the bloodstain sensitivity and the luminescence intensity may be affected. Accordingly, there is a limitation in use.

The same experiment was carried out for the Luminol reagent prepared by using sodium perborate as an oxidant, after only magnesium sulfate heptahydrate was added as a stabilizer according to a concentration. When 2.0 g/L of HEIDA was added to the L-MS1.0 formulation, pH changes as time passed were also observed.

Figure 9:
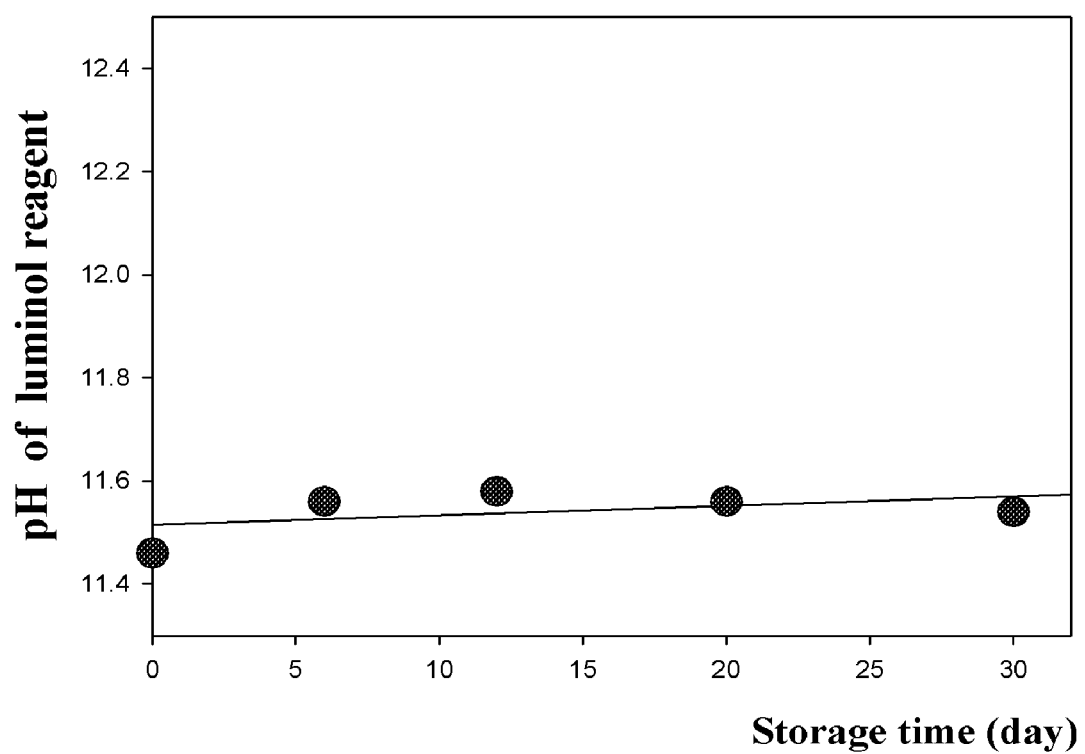
FIG. 9 is a graph showing pH changes of a Luminol reagent during storage caused by adding sodium perborate and magnesium sulfate heptahydrate.

Meanwhile, FIG. 9 shows pH changes after 2.0 g/L of HEIDA was added to the L-MS1.0 formulation and stored. As shown in the drawing, pH changes of the Luminol reagent rarely occurred. The above result confirmed that magnesium sulfate and HEIDA can be used simultaneously to stabilize hydrogen peroxide in the Luminol reagent.

Figure 10:
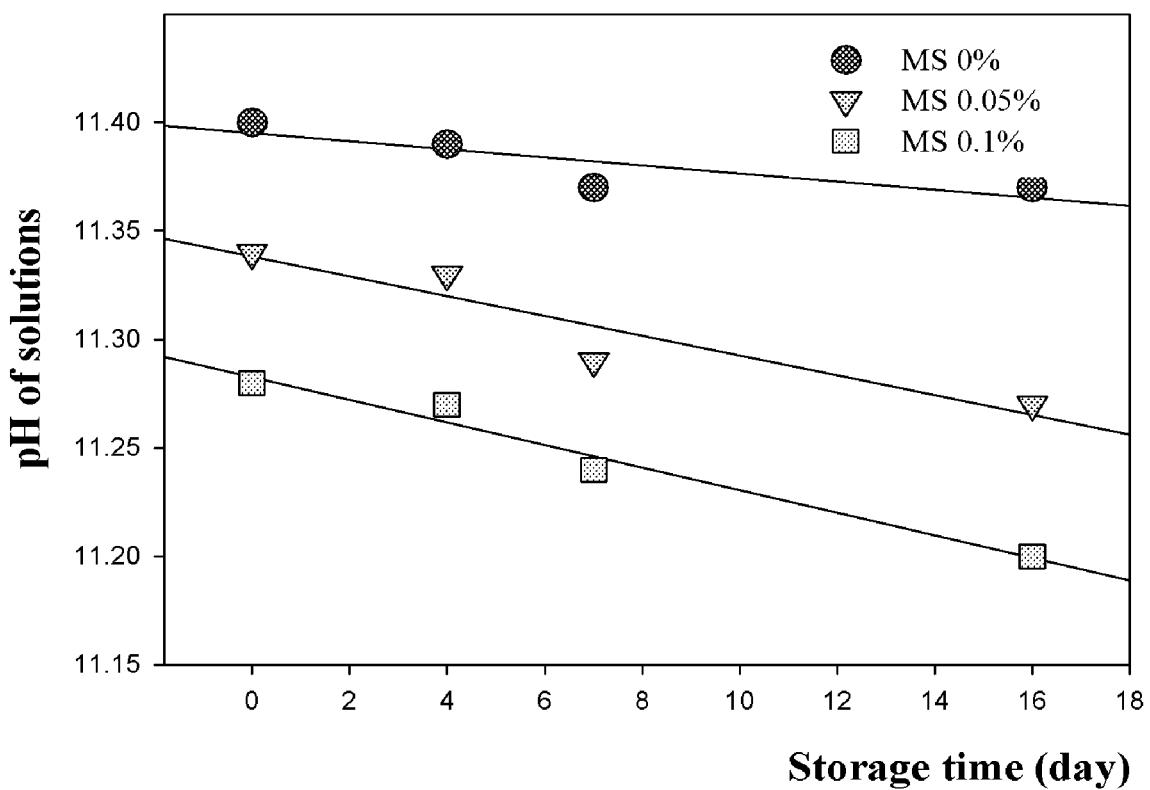
FIG. 10 is a graph showing pH changes during storage after adding HEIDA to an L-MS 1.0 formulation.

FIG. 10 shows pH changes according to a storage period of the Luminol reagent prepared by using sodium perborate instead of hydrogen peroxide as an oxidant and adding 0.5 g/L and 1.0 g/L of magnesium sulfate which is a hydrogen peroxide stabilizer.

When the storage period was increased, pH tended to be slightly decreased regardless of the added amount of magnesium sulfate, the Luminol reagent gradually turned into dark brown, and followed by changes in the bloodstain sensitivity. Accordingly, additional studies may be required. In addition, pH changes of Bluestar were not observed during storage.

pH Changes of Luminol Reagent According to Addition of Sodium Phosphate Dibasic

In order to minimize pH changes of the Luminol reagent after reaction with blood, 0 to 10 g/L of sodium phosphate dibasic used for preparation of an alkaline pH buffer solution was added to the L-SPB formulation, and then pH changes of the Luminol reagent were observed.

Figure 11:
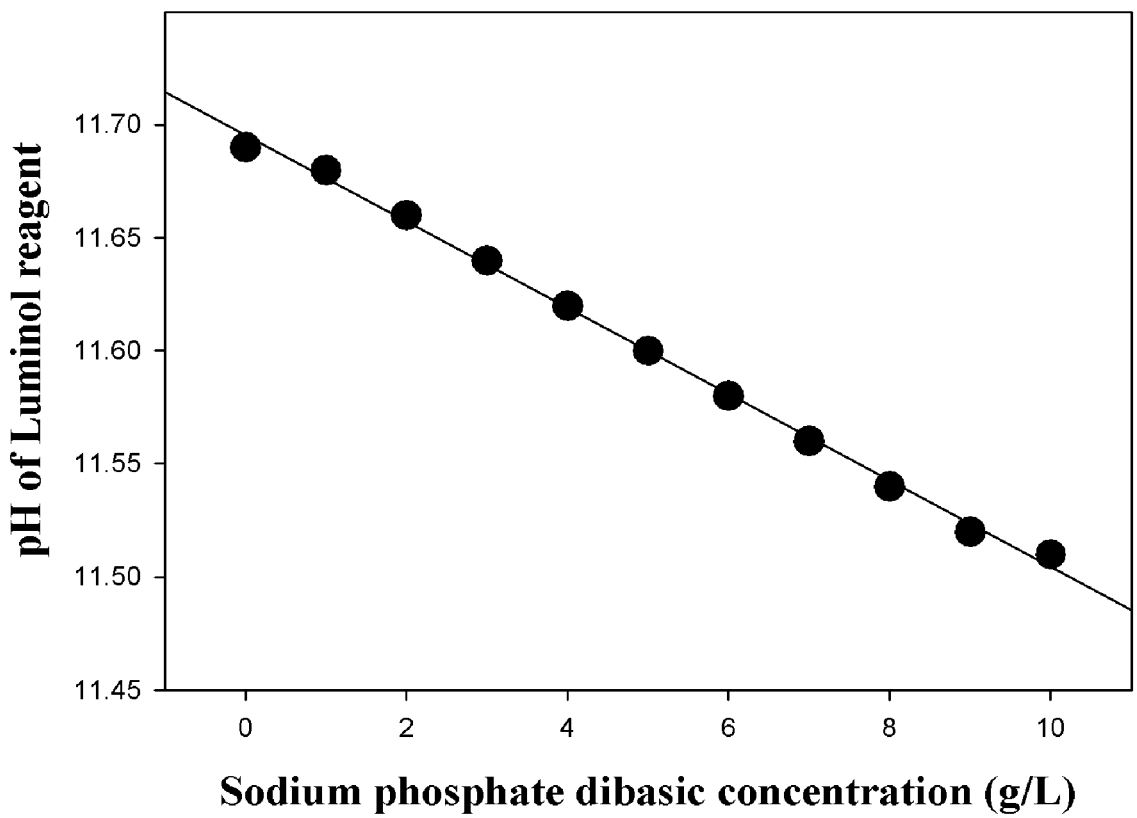
FIG. 11 is a graph showing pH changes of an L-SPB reagent caused by adding sodium phosphate dibasic heptahydrate.

FIG. 11 shows pH changes of the Luminol reagent according to the addition of sodium phosphate dibasic, in which rapid pH changes of the reagent did not occur subject to the addition of 10 g/L or less. Accordingly, sodium phosphate may be used to adjust pH upon preparing the Luminol reagent.

Changes of Sensitivity to Diluted Bloodstains of Luminol Reagent According to Storage Period Because the Luminol reagent has the bloodstain sensitivity rapidly decreased during storage, and is rarely possible to use while being stored after preparation, the Luminol reagent is required to be newly prepared whenever needed. On the contrary, it is known that Bluestar can be stored for a predetermined period after preparation. However, because there is no objective data on changes of the bloodstain sensitivity and the luminescence intensity according to storage period, changes of the bloodstain sensitivity and the luminescence intensity of the Luminol reagents during storage were observed in this experiment.

Changes in the bloodstain sensitivity according to time period of the Luminol reagent prepared by adding the hydrogen peroxide stabilizer were checked. In addition, changes in the bloodstain sensitivity according to time period were also observed after the Luminol reagent (L-SPB type) was prepared by adding sodium perborate as an oxidant instead of hydrogen peroxide.

Diluted blood samples of 1:10 to 1:10,000 were used to measure the bloodstain sensitivity. All the used diluted blood samples were obtained by dropping 100 µl of blood on paper discs by using a micropipette and dried at room temperature.

Six kinds of Luminol reagents prepared by adding the hydrogen peroxide stabilizer, Bluestar, a Luminol formulation used in the Korean National Police Agency, and a L-SPB formulation were used. In addition, changes in the sensitivity at the time of preparation and the sensitivity according to the storage were observed while L-MS1.0 and L-SPB prepared by adding 5 g/L of sodium phosphate dibasic being stored for 5 days.

FIGS. 12a, 12b, 12c, and 12d show changes in the sensitivity of the Luminol reagents during storage.

Although pH of Bluestar (11.4 to 11.8) was constantly maintained after preparation, the bloodstain sensitivity was significantly reduced during storage after preparation, and had no reaction with bloodstains after 9 days. Bluestar had the sensitivity to about 1:10,000 diluted bloodstains at the time of preparation. The Luminol reagent used in the Korean National Police Agency since 1990s had the sensitivity to 1:1,000 diluted bloodstain upon preparation, but had weak luminescence intensity only suitable for photographing in a dark room and had no reaction with bloodstains after 3 days.

Based on the results, it was determined that the Luminol reagent used in the KNPA may be usable within 1 day after preparation, and Bluestar may be usable for 1 or 2 days with storage.

The L-type had the bloodstain sensitivity of 1:10,000, but the luminescence intensity was slightly decreased after 9 days, and the bloodstain sensitivity was reduced to 1:1,000 by 10 times after 14 days. The six types of formulations, to which the hydrogen peroxide stabilizer was added, had the 1:10,000 bloodstain sensitivity upon preparation the same as that of the L-type.

L-MS0.3 and L-MS1.0 showed the same levels of the luminescence intensity and the bloodstain sensitivity as those at the time of preparation even after stored for 14 days. L-PPT2 and L-PPT10 tended to have the bloodstain sensitivity decreased more rapidly than that of the L-type. When 9 days were passed after preparation, the bloodstain sensitivity was 1:1,000, but the luminescence intensity was significantly low.

Based on the fact that the bloodstain sensitivity of L-PPT10 having slight pH changes during storage was more rapidly decreased than that of L-PPT2, it was found that potassium phosphate tribasic exerts some effects on the Luminol reagent and it is not preferable to use potassium phosphate tribasic as a hydrogen peroxide stabilizer.

L-SS2 and L-SS10 formulations prepared by adding sodium silicate as the hydrogen peroxide stabilizer showed the results similar to pH changes of the reagent during storage. L-SS2 showed levels of the bloodstain sensitivity and the luminescence intensity similar to those of the L-type, but L-SS10 maintained the bloodstain sensitivity of 1:10,000 even after 14 days.

Through the above experiments, it was confirmed that pH changes of the reagent during storage were closely related to changes in the luminescence intensity of the Luminol reagent and the bloodstain sensitivity during storage (FIGS. 5 to 7). Hydrogen peroxide may be required to be stabilized in advance to improve the stability of the Luminol reagent during storage after preparation Changes in Sensitivity of Luminol Reagent According to Addition of HEIDA to L-MS1.0

The L-MS 1.0 formulation was used to check the effect of HEIDA on the luminescence intensity and the bloodstain sensitivity during storage. The Luminol reagent was prepared by adding 2.0 g/L of HEIDA to the L-MS1.0 formulation and used in the experiment.

Figure 13A:
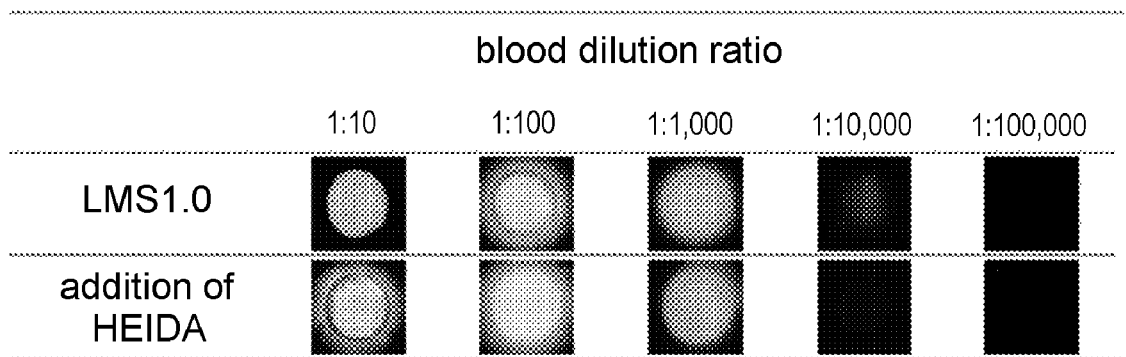
FIGS. 13a and 13b are images showing changes of the sensitivity of a Luminol reagent caused by adding HEIDA to L-MS 1.0.

As shown in FIG. 13a, the bloodstain sensitivity was slightly decreased due to the addition of HEIDA. Because the result of experiment was subject to the same pH condition, HEIDA may be a hydrogen peroxide stabilizer that negatively affects the sensitivity of the Luminol reagent.

Figure 13B:
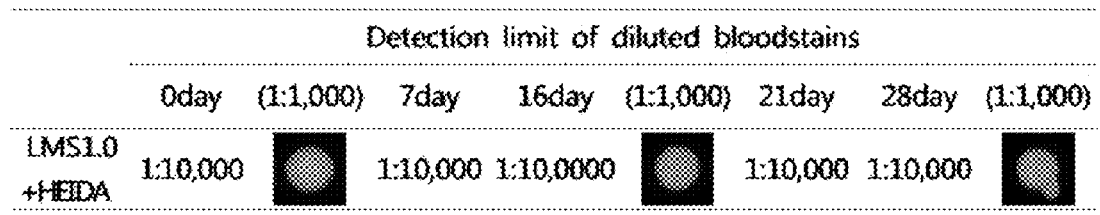

As shown in FIG. 8, pH changes of the Luminol reagent prepared by adding HEIDA to LMS1.0 were rarely observed during storage for 30 days. FIG. 13b shows changes in the sensitivity to diluted bloodstains when the same reagent was refrigerated. The sensitivity and the luminescence intensity to the diluted bloodstains were constantly maintained despite storage for 28 days. In other words, it was determined that the addition of HEIDA upon preparation of the Luminol reagent slightly reduces the bloodstain sensitivity of the ruminol reagent, but exerts no effect on changes in the sensitivity during storage of the reagent.

Changes in Sensitivity According to Storage Period of L-SPB Type

Figure 14A:
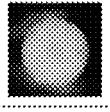
FIGS. 14a to 14c are images showing changes of the bloodstain sensitivity and the sensitivity according to a storage period of a Luminol reagent prepared by using sodium perborate instead of hydrogen peroxide as an oxidant.
Figure 14B:
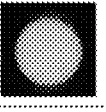
Figure 14C:
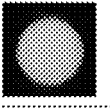

FIGS. 14a, 14b, and 14c show changes in the bloodstain sensitivity and the sensitivity according to storage period of the Luminol reagent prepared by using sodium perborate instead of hydrogen peroxide as an oxidant. As shown from the results, the addition of magnesium sulfate exerted no effect on the bloodstain sensitivity. Although the Luminol reagent obtained by using sodium perborate had the bloodstain sensitivity slightly higher than that of the Luminol reagent obtained by using hydrogen peroxide at the time of preparation, the bloodstain sensitivity was slightly decreased as time passed.

Figure 15A:
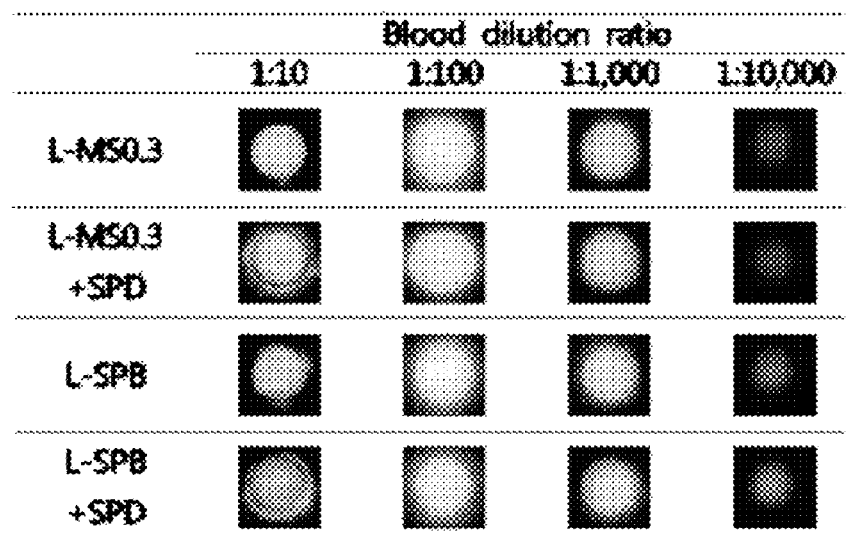
FIGS. 15a to 15c are images of the sensitivity to a diluted bloodstain while storing L-MS0.3 and L-SPB to which sodium phosphate dibasic heptahydrate is added, respectively.
Figure 15B:
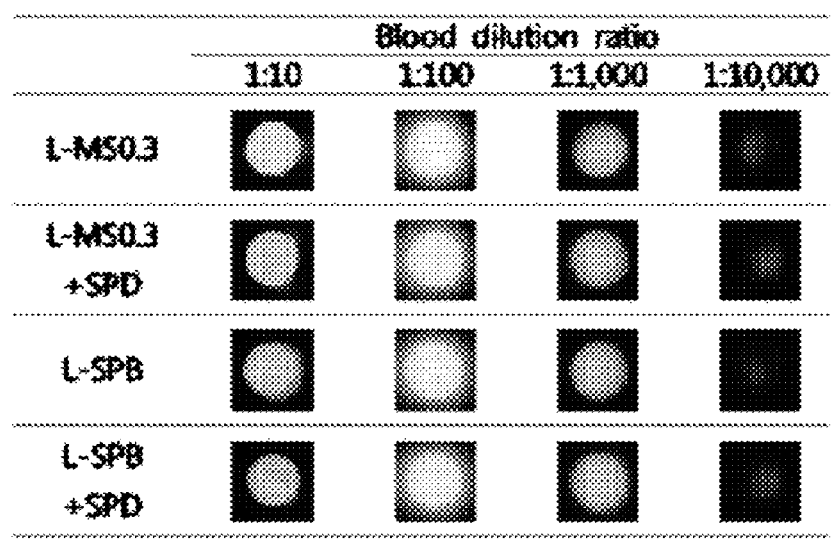
Figure 15C:
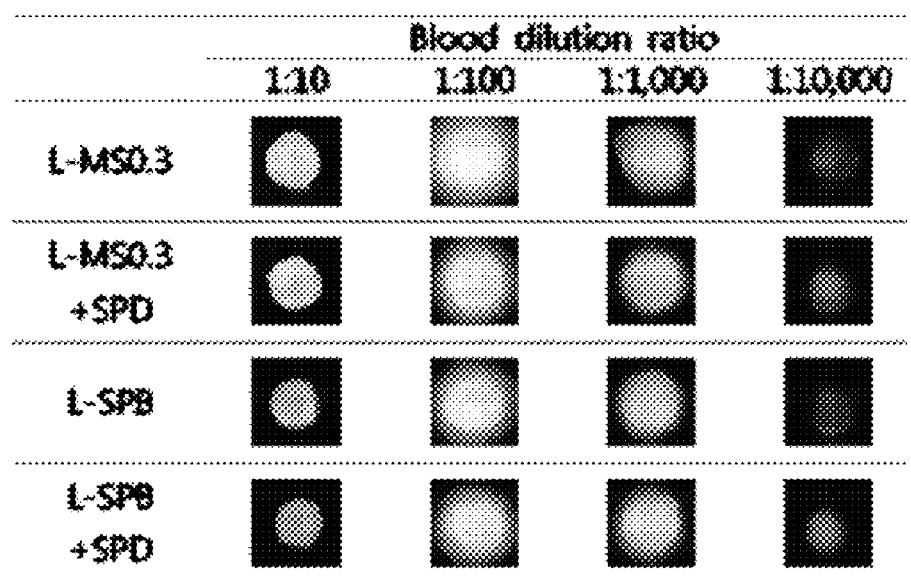

FIGS. 15a, 15b, and 15c show changes in the sensitivity to the diluted bloodstains after sodium phosphate dibsic at a 5 g/L content was added to L-MS0.3 and L-SPB with the same preparation method and stored for 5 days. All the four types of preparation methods had the similar bloodstain sensitivities of 1:10,000, and changes in the bloodstain sensitivity according to storage were not significant. Through the above results, it was found that the decrease of pH of the Luminol reagent by adding sodium phosphate dibasic exerts a slight effect on the bloodstain sensitivity of the reagent, and the addition of sodium phosphate dibasic does not significantly exert an effect on the stability of hydrogen peroxide or sodium perborate under an alkaline condition.

Specificity of Reagent

Because the Luminol reagent reacts with an iron component inside hemoglobin in blood, the Luminol reagent has the low specificity to human blood. In addition, because the Luminol reagent may react with various substances such as oxidants that may be present in crime scenes, the Luminol reagent is one of the reagents that require caution when used.

Luminol is not a reagent that only reacts with blood, and Luminol may be luminescent by reacting with various substances, such as a chemical oxidant, capable of oxidizing Luminol. Table 1 shows whether various Luminol reagents react with components of a vegetable, metal salt and bleach, respectively. As shown from the results, merely the luminescence intensity was different, and kinds of substances causing the reaction were all the same.

TABLE 1

|  | Luminol | Bluestar | LMS1.0 | LMS1.0 + HEIDA |
|---|---|---|---|---|
| Cucumber | ++ | + | + | + |
| Onion | + | + | + | + |
| Carrot | ++ | ++ | ++ | ++ |
| Cabbage | + | ++ | ++ | ++ |
| Young pumpkin | ++ | + | + | + |
| Mushroom | ++ | + | ++ | ++ |
| Green bean | + | + | ++ | ++ |
| Potato | + | + | + | + |
| Garlic | ++ | + | + | + |
| Sweet potato | + | + | + | + |
| Radish | +++ | +++ | +++ | +++ |
| $MnSO_4$ | no | no | no | no |
| $CuSO_4$ | ++++ | ++++ | ++++ | ++++ |
| $FeSO_4$ | ++++ | ++++ | ++++ | ++++ |
| Bleach solution | ++++ | ++++ | ++++ | ++++ |

In this experiment, actual reactions were checked after selecting 11 kinds of vegetables, four kinds of metal salts, and one type of bleach which are highly likely to cause an error reaction with Luminol.

After each substance was freshly stored in an E-tube, every 500 μl of the Luminol reagent was dispensed thereon. The specificity test was performed by using the luminescence intensity and the luminescence intensity observed with naked eyes.

The Luminol reagents used for the specificity test were Bluestar, Luminol used in the KNPA, L-MS1.0, and L-MS1.0+HEIDA. The substances used in the experiment were as follows.

Vegetables: cucumber, onion, cabbage, pumpkin, king oyster mushroom, pea, radish, garlic, carrot, potato, and sweet potato Metal salts: manganese sulfate ($MnSO_4$), copper sulfate ($CuSO_4$), iron sulfate ($FeSO_4$), and magnesium sulfate ($MgSO_4$)

Bleach (sodium hypochlorite, NaOCl 4% (w/v) or more)

It was observed that the Luminol reagents reacted with the vegetables had the luminescence which was weak but continuous for a long time. Because the luminescence intensity for the radish is relatively strong and continuous for a long time, it is required to be cautiously handled in the field.

Metal salts had the tendency opposite to that of vegetables, in which the luminescence intensity was very strong, but disappeared shortly after reaction.

In the case of a manganese salt, a brown precipitate was formed after reacted with the Luminol reagent, but no luminescent reaction was observed. The bleach containing sodium hypochlorite showed the luminescence intensity higher than that of the metal salt, but the reaction did not last for a long time.

Luminescence Persistency According to Preparation Method

Diluted blood samples of 1:100 were used to compare the luminescence persistency of the Luminol reagents prepared by each fabrication method with respect to bloodstains. Each 300 μl of the Luminol reagent was added to the diluted blood sample, and the duration at which the luminescence was observed with naked eyes was measured four times.

The luminescence persistency was checked through an average luminescence duration and a deviation. The preparation methods used in the experiment were Bluestar, Luminol used in the KNPA, L-type, L-MS1.0, and L-MS1.0+ HEIDA.

It was found from the above experimental results that the formulations, to which Bluestar and a hydrogen peroxide stabilizer are added, had the bloodstain sensitivity and the luminescence intensity superior to those of the conventional Luminol reagents. Table 2 shows the luminescence durations observed with the naked eyes and measured four times after the diluted bloodstain was reacted with the Luminol reagent.

TABLE 2

| | Chemiluminescence duration time (sec) | | | | | |
|---|---|---|---|---|---|---|
| | 1 | 2 | 3 | 4 | Average | SD |
| Luminol | 32 | 47 | 46 | 42 | 41.75 | 5.9 |
| Bluestar | 342 | 287 | 201 | 360 | 297.5 | 61.8 |
| L-MS1.0 | 313 | 314 | 306 | 353 | 321.5 | 18.4 |
| L-MS1.0 + HEIDA | 292 | 283 | 247 | 318 | 285 | 25.4 |

The average luminescence duration was 42 seconds for the Luminol reagent used in the KNPA, 297 seconds for Blustar, 321 seconds for L-MS1.0, and 285 seconds for L-MS1.0+HEIDA. The above result was similar to the result that the bloodstain sensitivity of the Luminol reagent was slightly decreased when HEIDA is added as a hydrogen peroxide stabilizer.

pH Changes of Luminol Reagent after Blood Reaction

Blood diluted by 1:5, 1:10, and 1:100 were used to check pH changes after blood reaction of the Luminol reagents prepared by each preparation method. Every 2 mL of blood diluted by 1:10 and 1:100 was added to 100 mL of the Luminol reagent, and agitated for 10 minutes, and pH changes were measured four times.

The Luminol reagents used in the experiment were Bluestar, Luminol used in the KNPA, L-type, L-MS1.0, and L-MS1.0+HEIDA. The same experiment was carried out for L-SPB type obtained by using sodium perborate instead of hydrogen peroxide as an oxidant after 2 mL of blood diluted by 1:5 and 1:10 was dropped on 100 mL of the Luminol reagent.

In order to check pH changes of the blood and the Luminol reagent according to addition of sodium phosphate dibasic, 5 mL of the blood diluted by 1:5 was mixed with 5 mL of the Luminol reagent and pH changes of the solution were measured as time passed for 5 days.

Figure 16A:
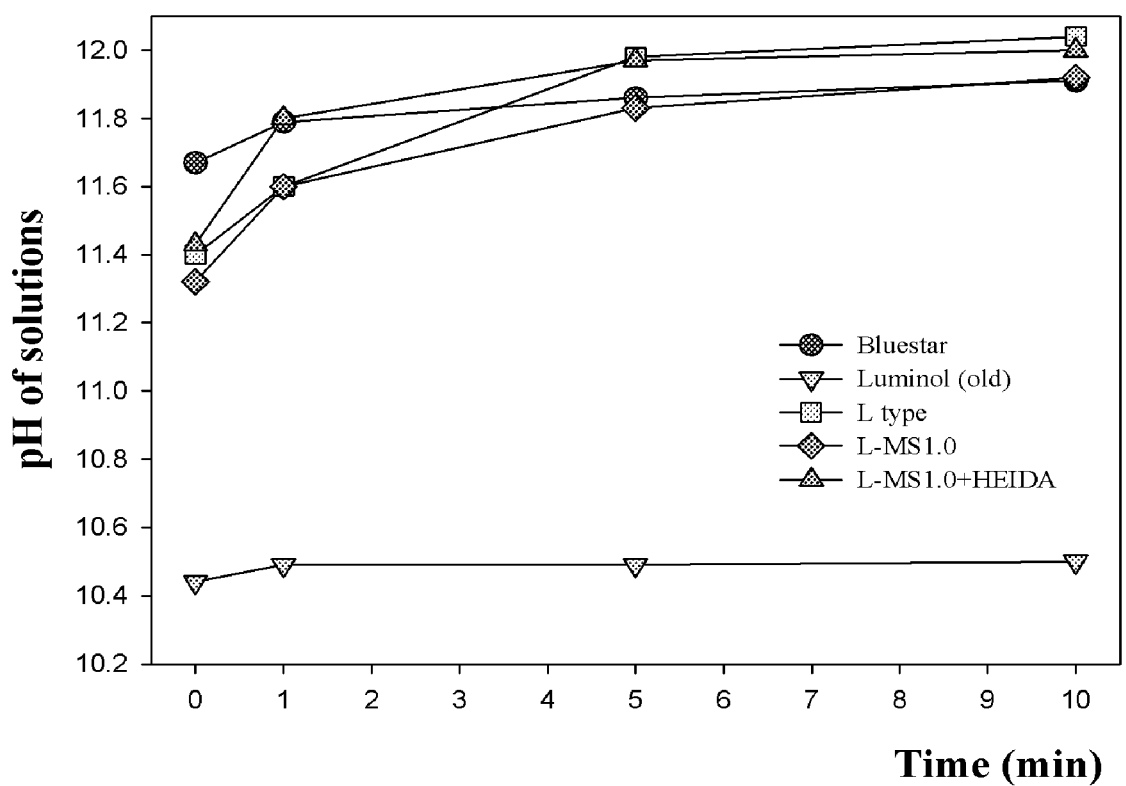
FIGS. 16a to 16d are graphs showing pH changes of a Luminol reagent according to a blood reaction.
Figure 16B:
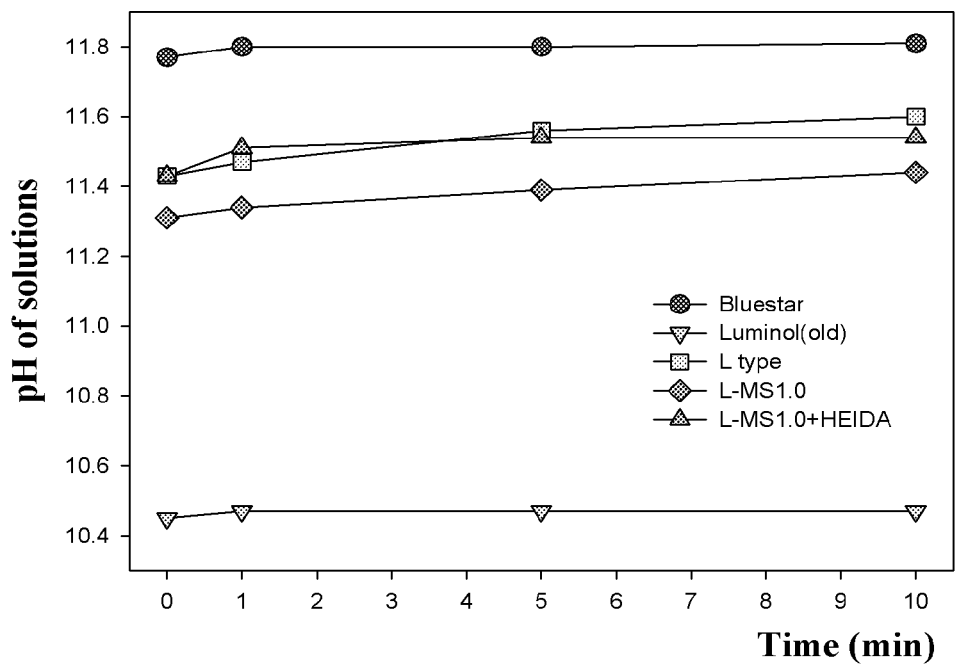

FIGS. 16a and 16b show pH changes of the Luminol reagent as time passed when 2 mL of diluted blood solution was mixed with 100 mL of Bluestar, Luminol used in the KNPA, L-type, L-MS1.0, and L-MS1.0+HEIDA. Whereas pH of Bluestar before reaction was 11.67 and pH after 10 minutes of the reaction was 11.81, which was increased by about 0.14, pH of L-type, L-MS1.0 and L-MS1.0+HEIDA were measured at 11.9 to 12.0 which was increased by 0.6 after the reaction.

Based on the Weber method and the previous study that a blood DNA damage caused by Bluestar was minimized, pH 12.2 or less may not affect blood DNA analysis.

Unlike mixed with 10-fold diluted blood solution, it was found that all the Luminol reagents had very low pH change ranges and each pH was changed into 0.1 or less when mixed with 100-fold diluted blood solution. Accordingly, it is presumed that the result was because the amount of hydrogen peroxide degraded due to the reaction with blood was small.

Figure 16C:
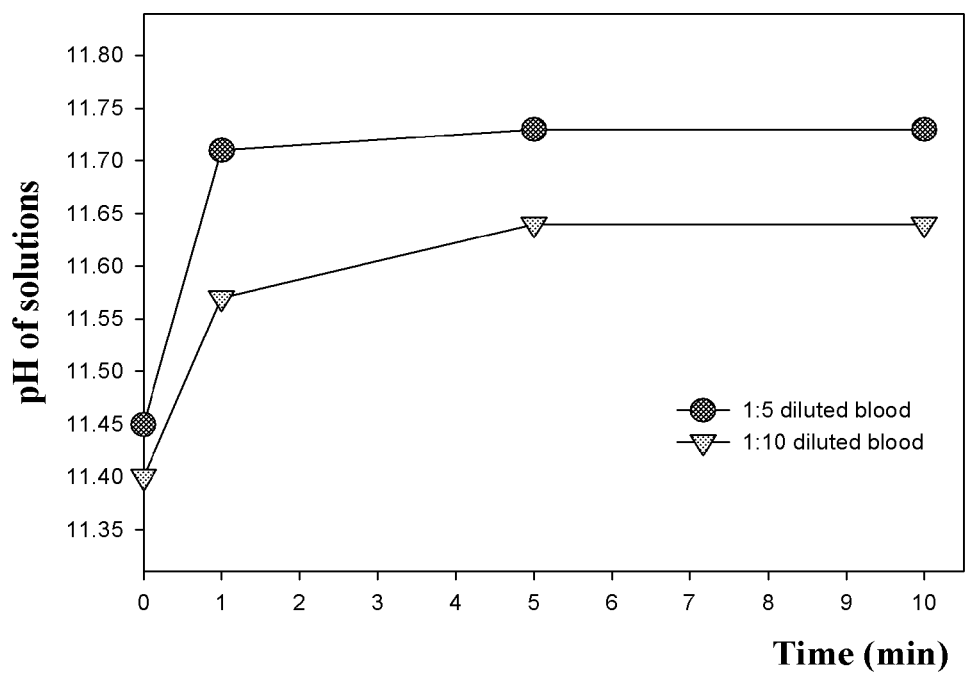

FIG. 16c shows pH changes of the reagent during 10 minutes after mixing 2 mL of diluted blood solution (1:5 and 1:10) to 100 mL of the L-SPB formulation. The pH was increased by 0.28 when the reagent was reacted with the 1:5 diluted blood solution, and the pH was increased by 0.24 when the reagent was reacted with the 1:10 diluted blood solution. Accordingly, the pH increase was slightly lower than that of the Luminol reagent prepared by using hydrogen peroxide as an oxidant.

If sodium perborate is used as the oxidant, pH may be further increased when the Luminol reagent is prepared. Accordingly, it is presumed that the luminescence intensity and the sensitivity to bloodstains may be further increased.

Figure 16D:
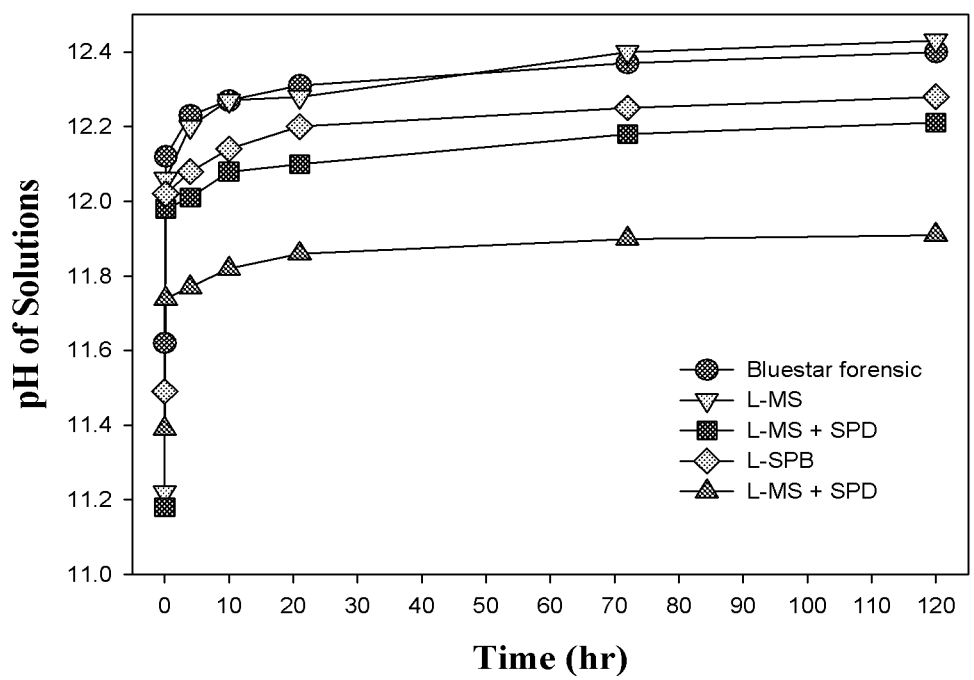

FIG. 16d shows pH changes of the mixture as time passed during storage for 5 days after 1:5 diluted blood and the Luminol reagent prepared by each preparation method were mixed with each other in a same amount (1:1).

Bluestar showed the pH change by 0.78 in which pH changed into 11.62 at the time of preparation, 12.12 after 10 minutes of reaction with blood, and 12.40 after 5 days. L-MS0.3 showed the pH change by 1.21 in which pH changed into 11.22 at the time of preparation, 12.06 after 10 minutes of reaction with blood, and 12.43 after 5 days. L-MS+SPD prepared by adding sodium phosphate dibasic to L-MS0.3 showed the pH change by 1.03 in which pH changed into 11.18 at the time of preparation, 11.98 after 10 minutes of reaction with blood, and 12.21 after 5 days.

L-SPB showed the pH change by 0.79 in which pH changed into 11.49 at the time of preparation, 12.08 after 10 minutes of reaction with blood, and 12.28 after 5 days. L-SPB+SPD prepared by adding sodium phosphate dibasic to L-SPB showed the pH change by 0.52 in which pH changed into 11.39 at the time of preparation, 11.74 after 10 minutes of reaction with blood, and 11.91 after 5 days.

Through the results of this experiment, it was confirmed that pH changes after reaction with blood were slightly lowered by adding sodium phosphite dibasic at the time of preparing the Luminol reagent. It was found that a pH increase of L-MS after reaction with blood was greater than that of Bluestar regardless of addition of sodium phosphate. However, L-SPB showed a pH change tendency similar to that of Bluestar when sodium phosphate was not added.

When 5 g/L of sodium phosphate is added to L-SPB, pH change after 5 days was 0.52 lower than that of Bluestar by 0.2 or more. Accordingly, the further study on a DNA destruction caused by adding sodium phosphate dibasic may be necessary.

Because final pH of the mixed solution after reaction with blood cannot be easily controlled by pH of the Luminol reagent, pH of the reagent is required to always be considered at the time of preparation, and the addition of a pH stabilizer such as sodium phosphate dibasic may be considered as an essential factor within a range of not affecting the bloodstain sensitivity.

The effect of the composition for detecting bloodstains according to the present invention on blood DNA was observed. Specifically, studies were performed on (i) the effect of chemical substances contained in the composition for detecting bloodstains according to the present invention on the DNA extraction efficiency, (ii) the effect on the degradation of blood DNA during storage after extraction, and (iii) the effect on DNA profile through STR amplification (PCR).

A Bluestar forensic kit was used as a control reagent.

Blood Samples and Bloodstain Test Reagent

The blood were obtained from three volunteers. Bluestar was purchased from Sirchie Company (Youngsville, USA) and prepared and used according to the user's manual.

A bloodstain detection reagent A (hereinafter referred to as 'Bloodflare A') and a bloodstain detection reagent B (hereinafter referred to as 'Bloodflare B') were prepared and used as follows.

Bloodflare A

After 1 L of distilled water and 3 g of sodium hydroxide were added to an empty container and completely dissolved, 1 g of Luminol was added and completely dissolved. Then, a storage solution was prepared by adding and dissolving 1 g of glycine, 5 g of sodium phosphate dibasic heptahydrate, and 0.3 g of magnesium sulfate. 1 mL of hydrogen peroxide per 100 mL of the storage solution was added and agitated.

Bloodflare B

After 1 L of distilled water and 3 g of sodium hydroxide were added to an empty container and completely dissolved, 1 g of Luminol was added and completely dissolved. Then, a storage solution was prepared by adding and dissolving 2 g of glycine and g of sodium phosphate dibasic heptahydrate. 1 g of sodium perborate monohydrate per 100 mL of the storage solution was added and agitated.

Effect on DNA Extraction Efficiency

The effects of bloodstain reagents on DNA extraction were probed by using a column scheme and a bead scheme which are typical DNA extraction methods.

The QIAAMP® DNA micro kit (Qiagen, Valencia, Calif.) was used for the column extraction scheme, and the QIA-SYMPHONY® DNA Investigator Kit (Qiagen) was used for the bead extraction scheme. Each kit was used according to user's manual.

Samples were prepared as follows, in which each of distilled water, Bluestar, Bloodflare A, and Bloodflare B were mixed with the same volume of a blood stock solution. DNA was extracted from each sample, and the extracted DNA was repeatedly quantified five times to calculate the average by using a NANODROP® 2000 (Thermo Fisher Scientific, Waltham, Mass., USA) spectrophotometer.

(i) a mixture of 25 µl of a blood stock solution (N=2) and distilled water, (ii) 25 µl of a blood stock solution (N=2) and Bluestar, (iii) 25 µl of a blood stock solution (N=2) and Bloodflare A, and (iv) 25 µl of a blood stock solution (N=2) and Bloodflare B.

The experimental results are summarized in Table 3 below. Referring to Table 3 below, it was found that the concentrations of DNA isolated from the samples were similar to each other, and all the bloodstain detection reagents used in this study did not affect the DNA extraction.

TABLE 3

| Sample | Prep. Method[a] | Conc. of DNA[b] | SD[c] |
|---|---|---|---|
| Blood + D.W[d] | Micro kit[e] | 11.5 | 0.7 |
| Blood + Bluestar | Micro kit[e] | 10.1 | 1.4 |
| Blood + BloodFlareA | Micro kit[e] | 10.3 | 0.6 |
| Blood + BloodFlareB | Micro kit[e] | 11.2 | 1.2 |
| Blood + D.W[d] | Investigator Kit[f] | 19.5 | 0.3 |
| Blood + Bluestar | Investigator Kit[f] | 19.0 | 0.5 |
| Blood + BloodFlareA | Investigator Kit[f] | 20.6 | 2.4 |
| Blood + BloodFlareB | Investigator Kit[f] | 19.2 | 0.7 |

[a]Preparation method;
[b]Concetration of DNA;
[c]Standard Deviation;
[d]Distilled Water
[e]QIAmp DNA micro kit;
[f]QIAsymphony DNA Investigator Kit Effect on Blood DNA Degradation In general, because the lower concentration of DNA, the more susceptible to environmental influences, blood stock solutions (N=3) were diluted to 1/10 and 1/100 using distilled water. Samples were prepared using 10 µl of diluted blood as follows. Herein, each of distilled water, Bluestar, Bloodflare A, and Bloodflare B was mixed with 10 µl of diluted blood in the same volume.

(i) a mixture of 10 µl of 1/10 diluted blood and distilled water, (ii) a mixture of 10 µl of 1/10 diluted blood and Bluestar, (iii) a mixture of 10 µl of 1/10 diluted blood and Bloodflare A, (iv) a mixture of 10 µl of 1/10 diluted blood and Bloodflare B, (v) a mixture of 10 µl of 1/100 diluted blood and distilled water, (vi) a mixture of 10 µl of 1/100 diluted blood and Bluestar, (vii) a mixture of 10 µl of 1/100 diluted blood and Bloodflare A, and (viii) a mixture of 10 µl of 1/100 diluted blood and Bloodflare B.

Each sample was incubated at room temperature for 0 day, 1 day, 3 days, and 7 days. The reaction time was applied after considering the time for storing the samples before analyzing the DNA profile from collecting an evidence by an investigation agency or the like.

DNA was extracted from every sample by using the QIAAMP® DNA micro kit and eluted by using 50 µl of a buffer AE included in the extraction kit.

In order to measure the degree of DNA degradation, Quantifiler™ Trio Quantification kit (Thermo Fisher Scientific) and ABI 7500 RT-PCR (Thermo Fisher Scientific) equipment which are real-time quantitative assay kits were used.

According to the conventional quantitative assay kits, a total human DNA target site is a single gene, and an amplification size is 62 bp (Quantifiler Human kit) or 140 bp (Quantifiler Duo kit). However, the Quantifiler™ Trio Quantification Kit has two types of total human DNA target sites, so that a large target site of 214 bp (Large Autosomal, LA) and a small target site of 80 bp (Small Autosomal, SA) in the amplification size can be simultaneously quantified.

The degradation index (DI) was calculated by dividing the large target site (Large Autosomal, LA) DNA concentration of the total human DNA by the small target site (Small Autosomal, SA) DNA concentration. The user's manual suggests criteria in that DNA is not degraded when the degradation index is less than 1, and the severe degradation has proceeded when the degradation index is more than 10.

Figure 17A:
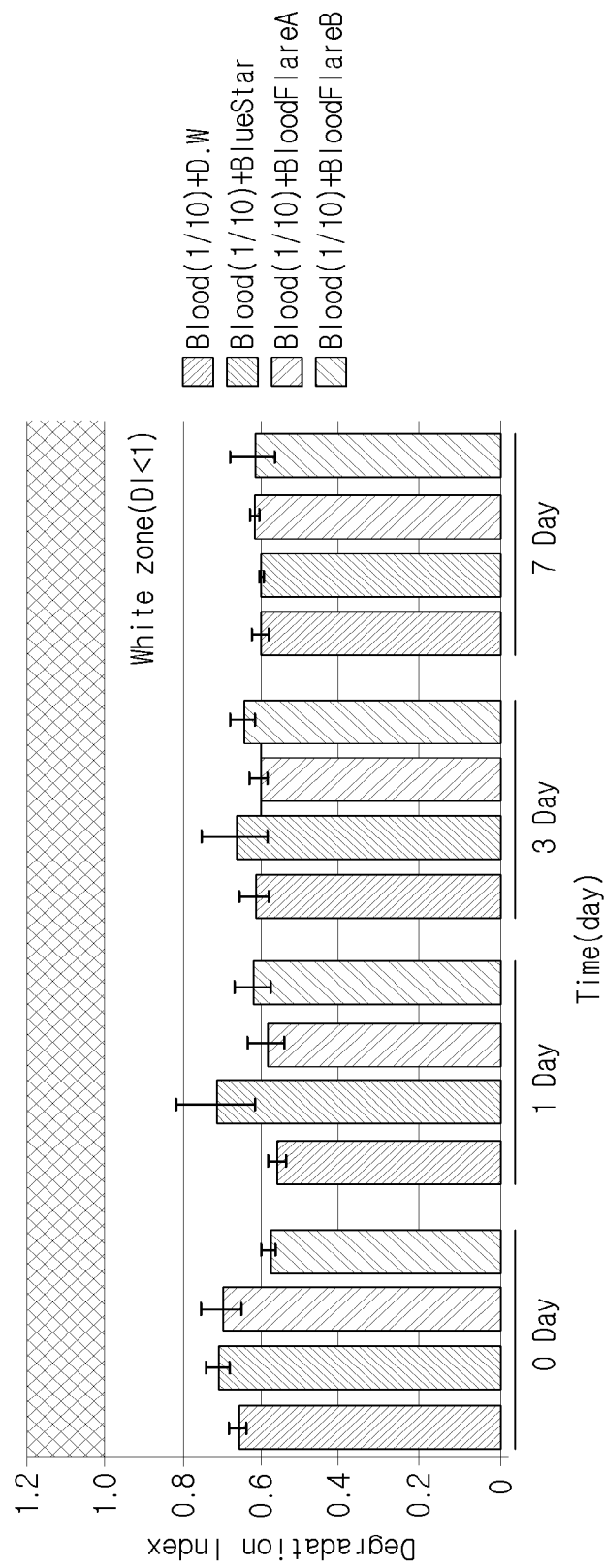
FIG. 17a is an image of effects on blood DNA degradation by samples obtained by mixing bloodstain detection reagents to 1/10 diluted blood.
Figure 17B:
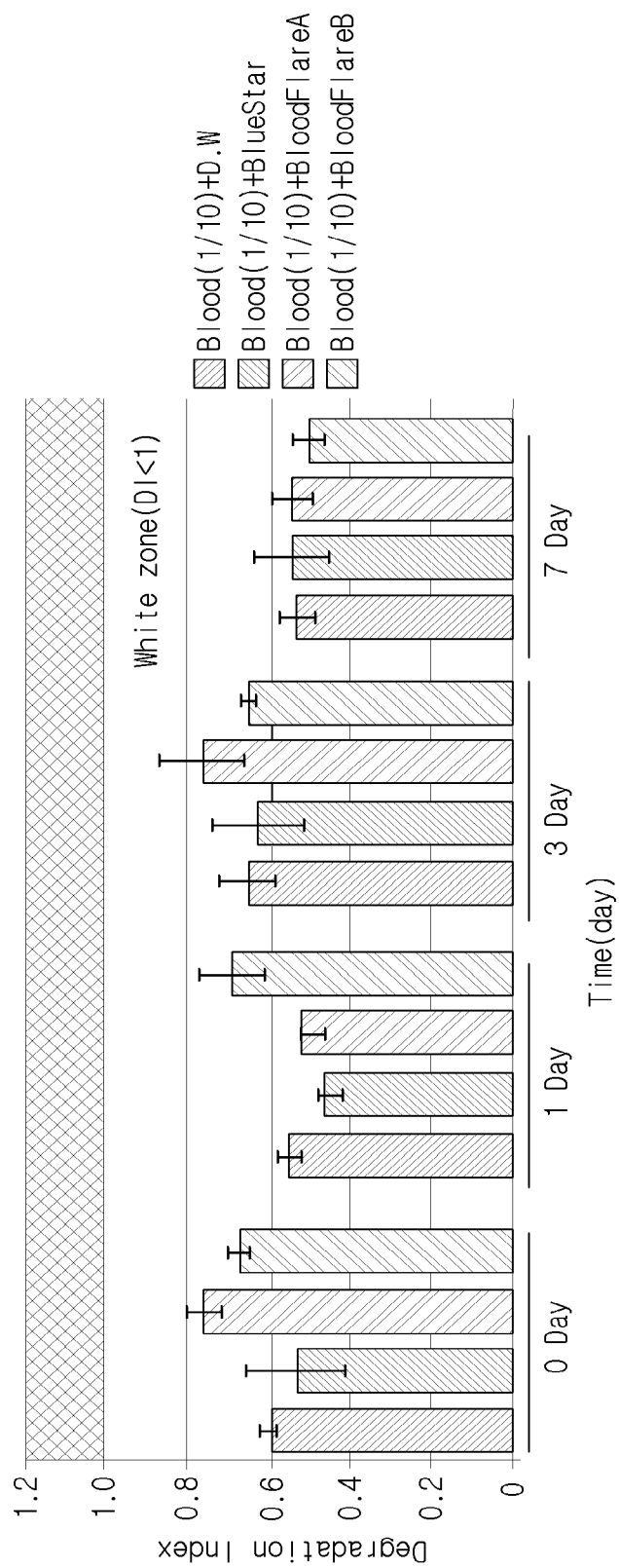
FIG. 17b is an image of effects on blood DNA degradation by samples obtained by mixing bloodstain detection reagents to 1/100 diluted blood.

According to the experimental result, although there were differences between the bloodstain detection reagents, all the degradation indexes showed figures less than 1, which was within insignificant level (FIGS. 17a and 17b). In other words, based on the criteria suggested in the user's guide, it was confirmed that all the bloodstain detection reagents used herein rarely exerted an effect on the DNA degradation.

Amplification and Capillary Electrophoresis

DNA, which was isolated from samples of 1/10 diluted blood reacted with the bloodstain detection reaction for 7 days among the prepared samples, was selected, and 10 µl was amplified by using the Identifier Plus kit (Thermo Fisher Scientific) as a template, so as to probe the effect on the blood DNA degradation.

The sample reacted with the bloodstain detection reagent for the longest time was firstly selected based on the criteria for selection. The 1/100 diluted blood had low overall DNA concentration, and the 1/100 diluted blood was excluded because variations between the samples were observed when only concentrations were compared. However, because the degradation index of the 1/100 diluted blood is obtained by calculating the ratio of LA DNA concentration to SA DNA concentration, no noticeable error was observed. Accordingly, the DI thereof was included in the above experimental results.

All experimental procedures were carried out according to the user's manual, the amplification was performed by using a GENEAMP® PCR System 9700 (Thermo Fisher Scientific), and the capillary electrophoresis was performed by using a 3500xL Genetic Analyzer (Thermo Fisher Scientific). Data analysis was performed on the basis of relative fluorescent units (RFU) 100 by using GENEMAPPER® ID-X v1.4 Software (Thermo Fisher Scientific).

Figure 18:
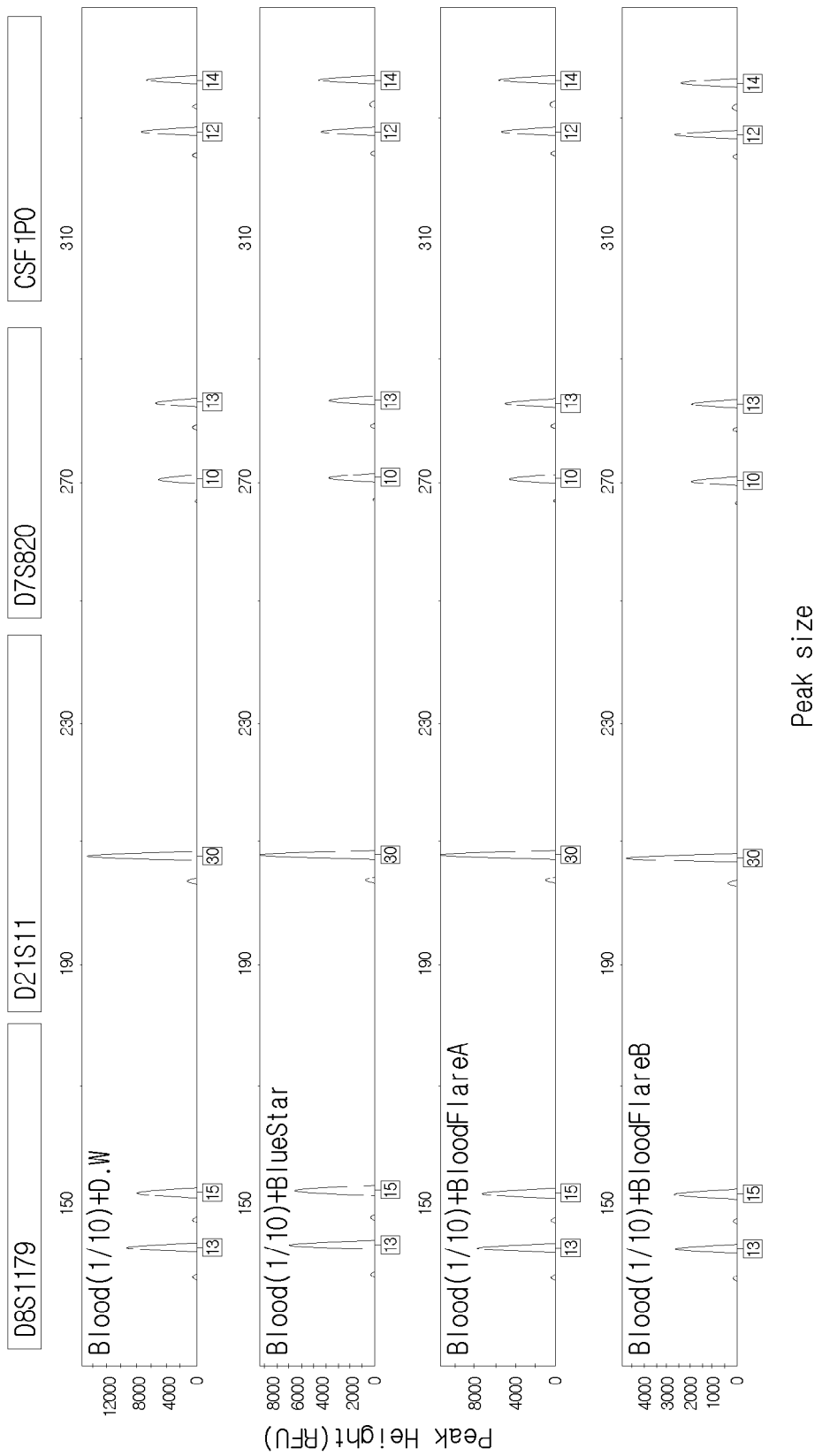
FIG. 18 is an image of effects on DNA profiles by bloodstain detection reagents.

Based on the calculation of the detection rates of DNA profiles in blood samples of the three volunteers, all of Bluestar, Bloodflare A, and Bloodflare B showed 100% detection rates (see FIG. 18).

In general, DNA degraded due to the exposure to various environments such as humidity, heat, and microorganisms induces fragmentation, and reduces an average size of an amplification product, and an amplified amount of the amplification product having a long length is decreased (or non-detected). This is called "ski slope effect", and often observed in the process of an STR analysis for the evidence in the crime scene. Although the detection rate of DNA profile is 100%, the presence of the ski slope effect due to the degradation caused by the bloodstain detection reagent was observed, and as a result, no ski slope effect was observed in all the reagents used in this study.

Although the present invention implemented by inventors is described in detail according to the above examples, the present invention is not limited to the examples and various modifications are available within the scope without departing from the invention.

What is claimed is:

1. A composition for detecting a bloodstain, the composition comprising:
   3-aminophthalhydrazide;
   glycine;
   sodium hydroxide; and
   sodium phosphate dibasic heptahydrate.

2. The composition of claim 1, further comprising:
   magnesium sulfate tetrahydrate; and
   hydrogen peroxide.

3. The composition of claim 1, further comprising sodium perborate monohydrate.

4. The composition of one of claim 1, wherein the composition has a hydrogen ion concentration (pH) which is 12.0 or less.

5. The composition of claim 4, wherein the hydrogen ion concentration (pH) is in a range of 11.3 to 11.7.

* * * * *